(12) United States Patent
Wariar et al.

(10) Patent No.: US 7,959,594 B2
(45) Date of Patent: Jun. 14, 2011

(54) ACCESS DISCONNECTION SYSTEMS AND METHODS

(75) Inventors: Ramesh Wariar, Tampa, FL (US); James Han, Palm Harbor, FL (US); George Lamberson, New Port Richey, FL (US); Thomas P. Hartranft, Clearwater, FL (US); Thore Falkvall, Helsingborg (SE)

(73) Assignees: Baxter International Inc., Deerfield, IL (US); Baxter Healthcare S. A., Glattpark (Opfikon) (CH)

( * ) Notice: Subject to any disclaimer, the term of this patent is extended or adjusted under 35 U.S.C. 154(b) by 1532 days.

(21) Appl. No.: 11/338,988

(22) Filed: Jan. 25, 2006

(65) Prior Publication Data

US 2006/0184087 A1  Aug. 17, 2006

Related U.S. Application Data

(63) Continuation of application No. 10/120,703, filed on Apr. 10, 2002, now Pat. No. 7,022,098.

(51) Int. Cl.
*A61M 37/00* (2006.01)
*C02F 1/44* (2006.01)

(52) U.S. Cl. ............ 604/6.16; 604/4.01; 604/5.01; 210/646; 210/746

(58) Field of Classification Search .......... 604/4.01, 604/5.01, 6.16; 210/646, 746
See application file for complete search history.

(56) References Cited

U.S. PATENT DOCUMENTS

| | | | |
|---|---|---|---|
| 3,682,162 A | 8/1972 | Colyer | |
| 3,731,685 A | 5/1973 | Eidus | |
| 3,759,261 A | 9/1973 | Wang | |
| 3,778,570 A | 12/1973 | Shuman | |
| 3,809,078 A | 5/1974 | Mozes | |
| 3,810,140 A | 5/1974 | Finley | |
| 3,814,249 A | 6/1974 | Eaton | |
| 3,832,067 A | 8/1974 | Kopf et al. | |
| 3,832,993 A | 9/1974 | Clipp | |
| 3,882,861 A | 5/1975 | Kettering et al. | |
| 3,900,396 A | 8/1975 | Lamadrid | |
| 3,946,731 A | 3/1976 | Lichtenstein | |
| 4,017,190 A | 4/1977 | Fischel | |
| 4,022,211 A | 5/1977 | Timmons et al. | |
| 4,026,800 A | 5/1977 | Friedrich et al. | |

(Continued)

FOREIGN PATENT DOCUMENTS

AU   199896231   3/1999

(Continued)

OTHER PUBLICATIONS

Extended European Search Report for European Application No. 10075482.9 mailed on Feb. 2, 2011.

*Primary Examiner* — Leslie R Deak
(74) *Attorney, Agent, or Firm* — K&L Gates LLP

(57) ABSTRACT

Apparatuses, devices, systems and methods for detecting access disconnection are provided. In one embodiment, a medical fluid system includes (i) a medical fluid machine and (ii) a device operable with the medical fluid machine, the device configured to provide electrical contact with a medical fluid, the device including (a) a tube used during dialysis therapy through which the medical fluid can flow, and (b) a conductive element configured to self-sealingly pierce the tube, the conductive element having a first portion exposed to the medical fluid and a second portion external to the tube.

9 Claims, 11 Drawing Sheets

U.S. PATENT DOCUMENTS

| | | |
|---|---|---|
| 4,055,496 A | 10/1977 | Friedrich et al. |
| 4,085,047 A | 4/1978 | Thompson |
| 4,087,185 A | 5/1978 | Lamadrid |
| 4,162,490 A | 7/1979 | Fu et al. |
| 4,166,961 A | 9/1979 | Dam et al. |
| 4,181,610 A | 1/1980 | Shintani et al. |
| 4,191,950 A | 3/1980 | Levin et al. |
| 4,192,311 A | 3/1980 | Felfoldi |
| 4,193,068 A | 3/1980 | Ziccardi |
| 4,231,366 A | 11/1980 | Schael |
| 4,231,370 A | 11/1980 | Mroz et al. |
| 4,327,731 A | 5/1982 | Powell |
| 4,353,368 A | 10/1982 | Slovak et al. |
| 4,366,051 A | 12/1982 | Fischel |
| 4,484,135 A | 11/1984 | Ishihara et al. |
| 4,484,573 A | 11/1984 | Yoo |
| 4,501,583 A | 2/1985 | Troutner |
| 4,534,756 A | 8/1985 | Nelson |
| 4,539,559 A | 9/1985 | Kelly et al. |
| 4,583,546 A | 4/1986 | Garde |
| 4,648,869 A | 3/1987 | Bobo, Jr. |
| 4,661,093 A | 4/1987 | Beck et al. |
| 4,710,163 A | 12/1987 | Butterfield |
| 4,739,492 A | 4/1988 | Cochran |
| 4,740,755 A | 4/1988 | Ogawa |
| 4,791,932 A | 12/1988 | Margules |
| 4,792,328 A | 12/1988 | Beck et al. |
| 4,796,014 A | 1/1989 | Chia |
| 4,846,792 A | 7/1989 | Bobo, Jr. et al. |
| 4,862,146 A | 8/1989 | McCoy et al. |
| 4,898,587 A | 2/1990 | Mera |
| 4,931,051 A | 6/1990 | Castello |
| 4,936,834 A | 6/1990 | Beck et al. |
| 4,959,060 A | 9/1990 | Shimomura et al. |
| 4,965,554 A | 10/1990 | Darling |
| 4,976,698 A | 12/1990 | Stokley |
| 4,977,906 A | 12/1990 | Di Scipio |
| 4,979,940 A | 12/1990 | Bobo, Jr. et al. |
| 4,981,467 A | 1/1991 | Bobo, Jr. et al. |
| 5,036,859 A | 8/1991 | Brown |
| 5,084,026 A | 1/1992 | Shapiro |
| 5,088,990 A | 2/1992 | Hivale et al. |
| 5,121,630 A | 6/1992 | Calvin |
| 5,137,033 A | 8/1992 | Norton |
| 5,139,482 A | 8/1992 | Simeon et al. |
| 5,197,958 A | 3/1993 | Howell |
| 5,247,434 A | 9/1993 | Peterson et al. |
| 5,264,830 A | 11/1993 | Kline et al. |
| 5,266,928 A | 11/1993 | Johnson |
| 5,291,181 A | 3/1994 | DePonte |
| 5,314,410 A | 5/1994 | Marks |
| 5,341,127 A | 8/1994 | Smith |
| 5,350,357 A | 9/1994 | Kamen |
| 5,354,289 A | 10/1994 | Mitchell et al. |
| 5,389,093 A | 2/1995 | Howell |
| 5,392,032 A | 2/1995 | Kline et al. |
| 5,395,358 A | 3/1995 | Lu |
| 5,416,027 A | 5/1995 | Baudin et al. |
| 5,435,010 A | 7/1995 | May |
| 5,439,442 A | 8/1995 | Bellifemine |
| 5,468,236 A | 11/1995 | Everhart et al. |
| 5,469,145 A | 11/1995 | Johnson |
| 5,486,286 A | 1/1996 | Peterson et al. |
| 5,487,827 A | 1/1996 | Peterson et al. |
| 5,510,716 A | 4/1996 | Buffaloe, IV et al. |
| 5,510,717 A | 4/1996 | Buffaloe, IV et al. |
| 5,522,809 A | 6/1996 | Larsonneur |
| 5,542,932 A | 8/1996 | Daugherty |
| 5,557,263 A | 9/1996 | Fisher et al. |
| 5,568,128 A | 10/1996 | Nair |
| 5,570,026 A | 10/1996 | Buffaloe, IV et al. |
| 5,570,082 A | 10/1996 | Mahgereffeh et al. |
| 5,603,902 A | 2/1997 | Maltais et al. |
| 5,644,240 A | 7/1997 | Brugger |
| 5,649,914 A | 7/1997 | Glaug et al. |
| 5,657,000 A | 8/1997 | Ellingboe |
| 5,670,050 A | 9/1997 | Brose et al. |
| 5,674,390 A | 10/1997 | Matthews et al. |
| 5,681,298 A | 10/1997 | Brunner et al. |
| 5,685,989 A | 11/1997 | Krivitski et al. |
| 5,690,610 A | 11/1997 | Ito et al. |
| 5,690,624 A | 11/1997 | Sasaki et al. |
| 5,702,376 A | 12/1997 | Glaug et al. |
| 5,702,377 A | 12/1997 | Collier, IV et al. |
| 5,744,027 A | 4/1998 | Connell et al. |
| 5,760,694 A | 6/1998 | Nissim et al. |
| 5,762,805 A | 6/1998 | Truitt et al. |
| 5,766,212 A | 6/1998 | Jitoe et al. |
| 5,790,035 A | 8/1998 | Ho |
| 5,790,036 A | 8/1998 | Fisher et al. |
| 6,663,585 B1 | 12/2003 | Ender |
| 2003/0036719 A1* | 2/2003 | Giacomelli et al. ......... 604/5.04 |
| 2003/0176829 A1* | 9/2003 | Lodi et al. .................... 604/4.01 |

FOREIGN PATENT DOCUMENTS

| | | |
|---|---|---|
| DE | 28 38 414 | 3/1980 |
| DE | 39 48 768 | 6/1981 |
| DE | 30 45 514 | 7/1982 |
| DE | 32 23 086 | 7/1983 |
| DE | 34 40 584 | 5/1986 |
| DE | 38 23 859 | 1/1990 |
| DE | 38 36 712 | 5/1990 |
| DE | 39 09 548 | 9/1990 |
| DE | 40 00 961 | 7/1991 |
| DE | 40 14 572 | 11/1991 |
| DE | 40 18 953 | 1/1992 |
| DE | 40 23 336 | 2/1992 |
| DE | 42 39 937 | 6/1994 |
| DE | 197 39 099 | 1/1999 |
| DE | 19 90 1078 | 2/2000 |
| EP | 270 048 | 6/1988 |
| EP | 328 162 | 8/1989 |
| EP | 328 163 | 8/1989 |
| EP | 332 330 | 9/1989 |
| EP | 0 542 140 | 5/1993 |
| EP | 0 551 043 | 7/1993 |
| EP | 0 590 810 | 4/1994 |
| EP | 0 611 228 | 8/1994 |
| EP | 0 745 400 | 12/1996 |
| EP | 0 820 776 | 1/1998 |
| EP | 0 835 669 | 4/1998 |
| EP | 0 895 787 | 2/1999 |
| EP | 0 911 044 | 4/1999 |
| FR | 2 680 678 | 5/1993 |
| FR | 2 737 124 | 1/1997 |
| GB | 2145859 | 3/1985 |
| GB | 2177247 | 1/1987 |
| GB | 2250121 | 5/1992 |
| JP | 4008361 | 1/1992 |
| JP | 6178789 | 6/1994 |
| JP | 10211278 | 8/1998 |
| JP | 11104233 | 4/1999 |
| JP | 11299889 | 11/1999 |
| JP | 2000-140092 | 5/2000 |
| TW | 249204 | 6/1995 |
| WO | WO 86/04710 | 8/1986 |
| WO | WO 94/02918 | 2/1994 |
| WO | WO 94/07224 | 3/1994 |
| WO | WO 96/25904 | 8/1996 |
| WO | WO 97/10013 | 3/1997 |
| WO | WO 98/32476 | 7/1998 |
| WO | WO 99/12588 | 3/1999 |
| WO | WO 99/26686 | 6/1999 |
| WO | WO 99/29356 | 6/1999 |
| WO | WO 99/42151 | 8/1999 |
| WO | WO 00/38761 | 7/2000 |
| WO | WO 01/06975 | 2/2001 |
| WO | WO 01/24854 | 4/2001 |
| WO | WO 01/47581 | 7/2001 |

* cited by examiner

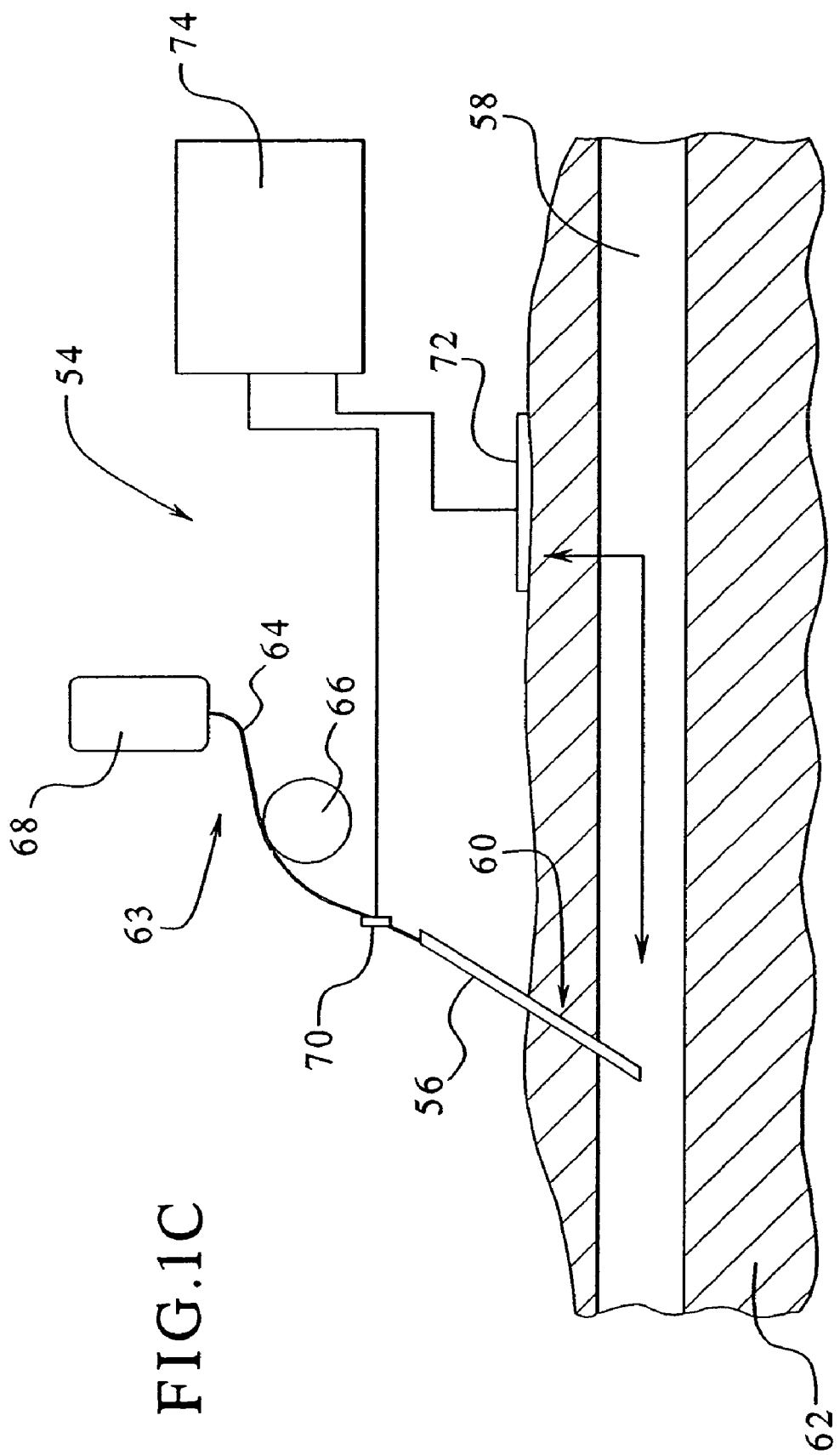

ACCESS DISCONNECTION SYSTEMS AND METHODS

PRIORITY

This application claims priority to and the benefit as a continuation application of U.S. patent application "ACCESS DISCONNECTION SYSTEMS AND METHODS," Ser. No. 10/120,703, filed Apr. 10, 2002 now U.S. Pat. No. 7,022,098.

BACKGROUND OF THE INVENTION

The present invention relates generally to patient access disconnection systems and methods for medical treatments. More specifically, the present invention relates to the detection of patient access disconnection, such as dislodgment of a patient access device during medical treatments or therapies including dialysis therapy.

A variety of different medical treatments relate to the delivery of fluid to and/or from a patient, such as the delivery of blood between a patient and an extracorporeal system connected to the patient via a needle or needles or any suitable access device inserted within the patient. For example, hemodialysis, hemofiltration and hemodiafiltration are all treatments that remove waste, toxins and excess water directly from the patient's blood. During these treatments, the patient is connected to an extracoporeal machine, and the patient's blood is pumped through the machine. Waste, toxins and excess water are removed from the patient's blood, and the blood is infused back into the patient. Needles or other suitable access devices are inserted into the patient's vascular access in order to transfer the patient's blood to and from the extracoporeal machine. Traditional hemodialysis, hemofiltration and hemodiafiltration treatments can last several hours and are generally performed in a treatment center about three to four times per week.

During any of these hemo treatments, dislodgment of the access device can occur, such as dislodgment of a needle inserted into the patient's vascular access including an arterio-venous graft or fistula. If not detected immediately, this can produce a significant amount of blood loss to the patient. The risks associated with a needle dislodgment are considerable. In this regard, important criteria for monitoring blood loss include, for example, the sensitivity, specificity and response time with respect to the detection of needle dislodgment. With increased levels of sensitivity, specificity, and response time, the detection of needle dislodgment can be enhanced, and blood loss due to dislodgment can be minimized.

Typically, patients undergoing medical treatment, such as hemodialysis, hemofiltration or hemodiafiltration, are visually monitored in order to detect needle dislodgment. However, the needle may not be in plain view of the patient or medical staff (i.e., it may be covered by a blanket) such that it could delay detection and, thus, responsive actions to be taken in view of dislodgment, such as stopping the blood pump of the extracorporeal machine to minimize blood loss to the patient.

Moreover, in view of the increased quality of life, observed reductions in both morbidity and mortality and lower costs than in-center treatments, a renewed interest has arisen for self care and home hemo therapies. Such home hemo therapies (whether hemodialysis, hemofiltration or hemodiafiltration) allow for both nocturnal as well as daily treatments. During these self care and home hemo sessions, especially during a nocturnal home hemo session, when the patient is asleep, dislodgment risks are more significant because nurses or other attendants are not present to detect the dislodgment.

Although devices that employ a variety of different sensors are available and known for detecting and/or monitoring a variety of different bodily fluids, these devices may not be suitably adapted to detect needle dislodgment. For example, known devices that employ sensors including pH, temperature and conductivity have been utilized to detect bedwetting and diaper wetness. Further, devices that employ pressure sensors and/or flow sensing devices are known and used during medical treatment, such as dialysis therapy, to monitor fluid flow including blood flow to and/or from the patient. However, these types of detection devices may not provide an adequate level of sensitivity and responsiveness if applied to detecting blood loss from the patient due to needle dislodgment. Although venous pressure is known to be used to monitor needle dislodgment, it is not very sensitive to needle drop-out.

Additional other devices and methods are generally known to monitor vascular access based on the electrical conductivity of blood. For example, Australian Patent No. 730,338 based on PCT Publication No. WO 99/12588 employs an electrical circuit which includes two points through which current is induced into blood flowing in an extracorporeal circuit that forms a closed conductor loop. Current is induced in blood using a coil that is placed around the outside of the tubing of the blood circuit. Thus, each coil does not directly contact the blood as it circulates through the tubing. In this regard, a current is generated into the blood flowing in the extracorporeal circuit by an alternating current that flows through one of the coils. The second coil is then utilized to measure a change in amperage of the induced current as it flows through the blood circuit.

In this regard, electrical current is coupled to a blood treatment system that includes a number of high impedance components, such a blood pump, air bubble traps, pinch clamps and/or the like. Because of the large impedance of the conducting fluid loop (due to the peristaltic pump and other components), the induction and detection of a patient-safe current requires an impractically complex design of the coil and system. Further, a high level of noise would necessarily result from the use of such levels of induced current. This can adversely impact the sensitivity of detection. If lower currents are used, the field coil would have to be increased in size to detect such low current levels. This may not be practical in use, particularly as applied during dialysis therapy.

PCT Publication No. WO 01/47581 discloses a method and device for monitoring access to the cardiovascular system of a patient. The access monitoring employs an electrical circuit which can generate and detect a current at separate points along a blood circuit connected to the patient. Current is injected into blood using capacitive couplers that each have a metal tube placed around the blood circuit tubing. In this regard, the metal tube defines a first plate of a capacitor; the blood circuit tubing defines the dielectric; and the blood inside of the blood circuit tubing defines the second plate of the capacitor.

The generator applies a potential difference between a pair of capacitive couplers to generate a current in blood flowing through the blood circuit. A detector utilizes an additional and separate pair of capacitive couplers to measure the current along at least one section of the venous branch between a first contact point and the venous needle. The change in voltage (dV) can then be determined based on a measured change in current and compared to a reference range (I) to monitor access conditions. In this regard, PCT Publication No. WO 01/47581 requires a complex circuit design that utilizes multiple sets of capacitive couplers to monitor vascular access conditions. This can increase the cost and expense of using same.

Further, the mere use of capacitive coupling to inject an electric signal in the blood circuit and/or for detection purposes can be problematic. In this regard, the signal must pass through the tubing of the blood circuit as the tubing acts as a dielectric of the capacitor. This may cause an excess level of noise and/or other interference with respect to the detection of changes in vascular access conditions.

In this regard, it is believed that known devices, apparatuses, systems, and/or methods that can be used to monitor a patient's access conditions may not be capable of detecting change in access conditions, such as in response to needle drop out, with sufficient sensitivity and specificity to ensure immediate detection of blood loss such that responsive measures can be taken to minimize blood loss. As applied, if twenty seconds or more of time elapses before blood loss due to, for example, dislodgment of the venous needle, over 100 milliliters in blood loss can occur at a blood flow rate of 400 ml/min, which is typical of dialysis therapy. Thus, the capability to respond quickly upon immediate detection of dislodgment of an access device, such as a needle, from a patient is essential to ensure patient safety.

Accordingly, efforts have been directed at designing apparatuses, devices, systems and methods for detecting changes in access conditions, such as in response to needle dislodgment, wherein detection is sensitive, specific and immediate in response to such access changes such that responsive measures can be suitably taken to minimize blood loss from the patient due to same.

SUMMARY OF THE INVENTION

The present invention provides improved devices, apparatuses, systems, and methods for detecting dislodgment or disconnection of an access device, such as dislodgment of a needle inserted in a patient during dialysis therapy. The devices, apparatuses, systems, and methods of the present invention utilize an electrical circuit with a number of electrical contacts which are in fluid contact with the fluid circuit such that an electrical signal can be injected into at least a segment including, for example, a loop defined along at least a portion of the conducting fluid circuit. In this regard, a direct-contact measurement can be used to provide immediate detection of a change in an electrical value in response to a change in access conditions, such as a change in impedance due to dislodgment of a needle or other access device from the patient during medical therapy including, for example, dialysis therapy and medication delivery.

An advantage of the present invention is to provide an improved device, apparatus, system and/or method for detecting access disconnection.

A further advantage of the present invention is to provide an improved device, apparatus, system and/or method for detecting dislodgment of an access device from a patient during medical therapy including dialysis therapy.

Another advantage of the present invention is to provide an improved device, apparatus, method and/or system for detecting needle drop-out during dialysis therapy.

Yet another advantage of the present invention is to provide a sensitive, specific and responsive apparatus and/or device for detecting access disconnection during selfcare and home hemo treatments.

Moreover, an advantage of the present invention is to provide a viable device or apparatus for allowing a patient to self administer or other non-medical personnel in a non-medical facility a dialysis therapy that uses a portion of the patient's circulatory system.

Still further, an advantage of the present invention is to provide an improved apparatus for detecting access disconnection that uses a direct conductivity measurement.

Yet still further, an advantage of the present invention is to provide an access disconnection detection device, method and/or system that employs an electrical circuit in fluid and electrical contact with blood flowing through a blood circuit allowing direct conductivity measurements to be made.

Furthermore, an advantage of the present invention is to provide an improved device, system and method for monitoring and/or controlling blood loss from a patient.

Another advantage of the present invention is an improved method for dialysis that employs an apparatus, device and/or system capable of detecting access disconnection, such as dislodgment of a needle inserted into a patient through which blood flows during dialysis therapy and minimizing any resulting blood loss.

Yet another advantage of the present invention is an improved device for connecting an electrical contact to a fluid circuit allowing fluid and electrical communication between the electrical contact and fluid flowing through the fluid circuit.

Still another advantage of the present invention is an improved apparatus, device, system and/or method for detecting access disconnection, such as needle drop-out during dialysis therapy, with enhanced sensitivity, accuracy and responsiveness.

Yet still another advantage of the present invention are improved apparatuses, devices, systems and/or methods for the detection of fluid loss due to, for example, dislodgment of a single access device during medical therapies, for example, medication delivery and single needle hemo therapies.

Additional features and advantages of the present invention are described in, and will be apparent from, the following Detailed Description of the Invention and the figures.

BRIEF DESCRIPTION OF THE FIGURES

FIG. 1C illustrates a perspective view of an embodiment of the present invention showing access disconnection detection capabilities during medical therapies administered via a single needle.

DETAILED DESCRIPTION OF THE INVENTION

Figure 1A:
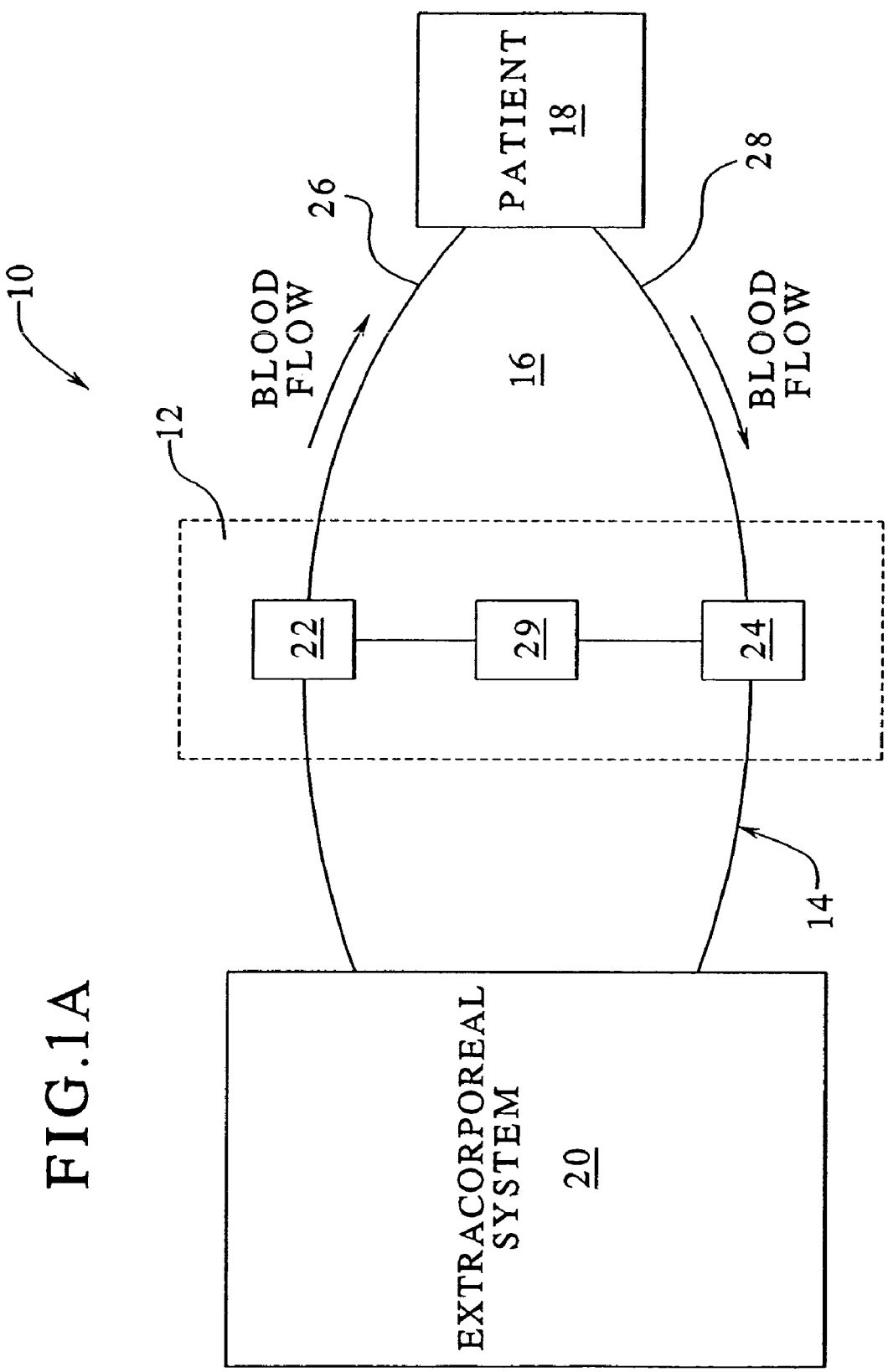
FIG. 1A illustrates a schematic view of an embodiment of the present invention showing two needles insertable within a patient through which blood flows to and from an extracorporeal system.

The present invention provides medical devices, apparatuses, systems and methods for detecting access disconnection. More specifically, the present invention provides medical devices, apparatuses, systems, and methods that employ, in part, an electrical circuit with electrical contacts in fluid contact and electrical communication with a fluid circuit allowing a direct conductivity measurement to be used such that dislodgment of a needle or other access device through which fluid flows between a patient and the fluid circuit can be immediately detected. In this regard, fluid loss (i.e., blood loss) due to, for example, dislodgment of a needle from a patient undergoing medical treatment, such as dialysis therapy, medication delivery or the like, can be controllably minimized.

It should be appreciated that the present invention is not limited to the detection of needle dislodgment but can be utilized to detect the dislodgment or disconnection of any suitable access device. As used herein, the term "access disconnection" or other like terms means any suitable condition or event which can cause a loss or leak of an electrically conductive fluid flowing along a fluid circuit connected to the patient provided that a change in the electrical continuity between electrical contacts coupled to the fluid circuit can be detected. It should be appreciated that a change in the electrical continuity as measured by an electrical value, such as impedance, may be detected even in the absence of dislodgment of an access device from the patient. The term "access device" as used herein or other like terms means a suitable device that can be inserted within a patient such that fluid, including blood, can pass to, through and/or from the patient via the access device. The access device can include a variety of different and suitable shapes, sizes and material make-up. Examples of an access device includes needles, catheters, cannulas or the like. The access device can be composed of any suitable material including, for example, stainless steel, plastic or like biocompatible materials.

Although in the embodiment set forth below the apparatus and/or device is designed for use in a dialysis therapy, such as hemodialysis, hemofiltration or hemodiafiltration, it should be noted that the present invention can be used in a number of different medical therapies that employ a variety of different and suitable fluid systems, such as extracorporeal blood systems. For example, the invention of the present application can be used during intravenous infusion that can employ the use of a single needle insertable within the patient for delivering a medical solution or drug, blood, blood products, processed blood or the like between the patient and the fluid system. In addition, the present invention can be used in plasma exchange therapies, where a membrane is used to separate whole blood into plasma and cellular components.

With respect to dialysis therapy, the present invention can be used in a variety of different therapies to treat kidney failure. Dialysis therapy as the term or like terms are used throughout the text is meant to include and encompass any and all forms of therapies that utilize the patient's blood to remove waste, toxins and excess water from the patient. Such therapies include both intermittent, including hemodialysis, hemofiltration and hemodiafiltration, and continuous therapies used for continuous renal replacement therapy (CRRT). These continuous therapies include slow continuous ultrafiltration (SCUF), continuous veno venous hemofiltration (CVVH), continuous veno venous hemodialysis (CVVHD), and continuous veno venous hemodiafiltration (CVVHDF). Dialysis therapy can also include peritoneal dialysis, such a continuous ambulatory peritoneal dialysis, automated peritoneal dialysis and continuous flow peritoneal dialysis. Further, although the present invention, in an embodiment, can be utilized in methods providing a dialysis therapy for patients having chronic kidney failure or disease, it should be appreciated that the present invention can be used for acute dialysis needs, for example, in an emergency room setting. Lastly, as one of skill in the art appreciates, the intermittent forms of therapy (i.e., hemofiltration, hemodialysis and hemodiafiltration) may be used in the in center, self/limited care as well as the home settings.

In an embodiment, the present invention includes an electrical circuit with a number of electrical contacts, preferably a pair of electrical contacts, in fluid contact and electrical communication with the fluid circuit. The electrical contacts can include any suitable device through which electrical connection can be made with the fluid circuit thereby defining a conductive pathway or conductor loop therein. Changes in an electrical value or any suitable parameter associated with the conductor loop can then be monitored in response to changes in access conditions as described below. In an embodiment, the electrical contact includes an electrode which can be coupled to the fluid circuit such that an electrical connection can be made in fluid contact with fluid flowing through the fluid circuit as discussed below.

For example, a constant current or other suitable electrical signal can be injected into the fluid circuit via an electrode pair in contact with fluid flowing between the electrodes thereby defining a loop along at least a portion of the fluid circuit. A change in an electrical value, preferably impedance, can then be measured in response to access disconnection. This can provide a direct conductivity measurement capable of detecting a change in impedance or other suitable electrical parameter of the fluid, such as an electrically conductive fluid including blood, medical solutions or the like, as it flows between a patient and a fluid system (i.e., an extracorporeal blood system) via a needle, needles or other access device(s) inserted within the patient.

In this regard, the present invention can effectively detect dislodgment of a needle (e.g., a venous needle and an arterial needle) or other access device through which blood or other suitable fluid can flow, for example, to, through and from the patient, such as a blood circuit used during dialysis therapy. The detection capability of the present invention is believed to be immediate based on the measurable change in, for example, impedance of the electrically conductive fluid or fluids due to fluid loss resulting from disconnection of the access device from the patient.

The immediate detection capabilities of the present invention are important, particularly as applied to dialysis therapy where a significant amount of blood loss can occur within a relatively short period of time if delays in detection and responsive actions to stop the blood loss occur. Under typical dialysis conditions, if 20 seconds or more time elapses before blood loss due to dislodgment is detected and stopped, over 100 milliliters of blood can be lost based on typical blood flow rates of 400 milliliters/minute.

Applicants have discovered that the present invention can detect access disconnection, particularly in response to venous needle dislodgment during dialysis therapy, with a high degree of sensitivity and specificity in addition to its immediate detection capabilities. The direct-contact measurement of the present invention is capable of detecting a change of an electrical value, preferably impedance, due to needle dislodgment or the like as the blood flows through the blood circuit during dialysis therapy. As used herein, the term "electrical value" or other like terms means any suitable electrical parameter typically associated with electrical circuitry including, for example, impedance, resistance, voltage, current, rates of change thereof and combinations thereof. The detection of a change in impedance or the like is an indication that the needle has become dislodged or other like condition has occurred. It is noted that the detection capabilities of the present invention can also effectively detect blood loss during medical therapy even if the needle or needles have not become dislodged or at least not entirely dislodged. In this regard, the present invention can be effectively utilized to controllably minimize blood loss from the patient based on the ability of the present invention to immediately measure a change in impedance or the like due to blood loss with a high degree of sensitivity and specificity.

The devices and apparatuses of the present invention can include a variety of different components and configurations depending on the applied medical therapy such that fluid loss, particularly blood loss due to needle dislodgment or the like, can be effectively monitored.

Multiple Access Disconnection

Referring now to FIG. 1A, an embodiment of the apparatus 10 of the present invention includes a pair of electrical contacts 12 in fluid contact with a blood tubing set 14 of a blood circuit 16. The blood circuit 16 connects a patient 18 to an extracorporeal blood system 20 as applied to, for example, dialysis therapy including hemodialysis, hemofiltration, hemodiafiltration, continuous renal replacement or the like or plasma therapies. The pair of electrical contacts 12 includes a first electrical contact 22 and a second electrical contact 24 which are attached to a respective first tube member 26 and second tube member 28 of the blood circuit 16. The first tube member 26 is connected to a venous needle or other suitable access device inserted into a vascular access region (not shown) of the patient. The second tube member 28 is connected to an arterial needle or the like also inserted into a vascular access region (not shown) of the patient. During dialysis therapy, for example, blood flows from the patient 18 through the arterial needle to the extracorporeal blood system 20 includes, for example, a dialysis machine, via the second tube member 28 where the blood is treated and delivered to the patient 18 through the venous needle via the first tube member 26.

As the blood flows through the blood circuit during dialysis therapy, a constant electric current or the like generated by a controller 29 can be injected or passed into the flowing blood via the electrical contact pair, preferably an electrode pair as described below. The electrode pair connected to the controller 29 or other suitable electronic device can then be used to measure a voltage change across an unknown fluid (e.g., blood) impedance or other like electrical value to detect a change in impedance or the like across the vascular access region. In an embodiment, one electrode can be used to inject the electrical signal into the fluid circuit while the other electrode of the pair can be used to sense a change in the electrical value and pass an electrical signal indicative of the same to the controller for processing and detection purposes. Upon dislodgment of at least one of the venous needle and arterial needle from the blood circuit or other suitable condition, an immediate and detectable increase in impedance or the like can be measured as compared to the impedance or other suitable parameter measured under normal operating conditions.

It should be appreciated that the present invention as embodied in FIG. 1A can be modified in a variety of suitable ways depending on the medical therapy as applied. For example, the venous and arterial needles can be inserted into the vascular access of the patient on any suitable part of the patient's body, such as the upper arm, lower arm, upper thigh area or the like during dialysis therapy. As previously discussed, the present invention can be applied to a variety of different medical therapies including intravenous infusions, plasma exchanges, medication delivery, drug delivery, blood delivery and dialysis therapies (i.e., hemofiltration, hemodialysis, hemodiafiltration and continuous renal replacement).

Figure 1B:
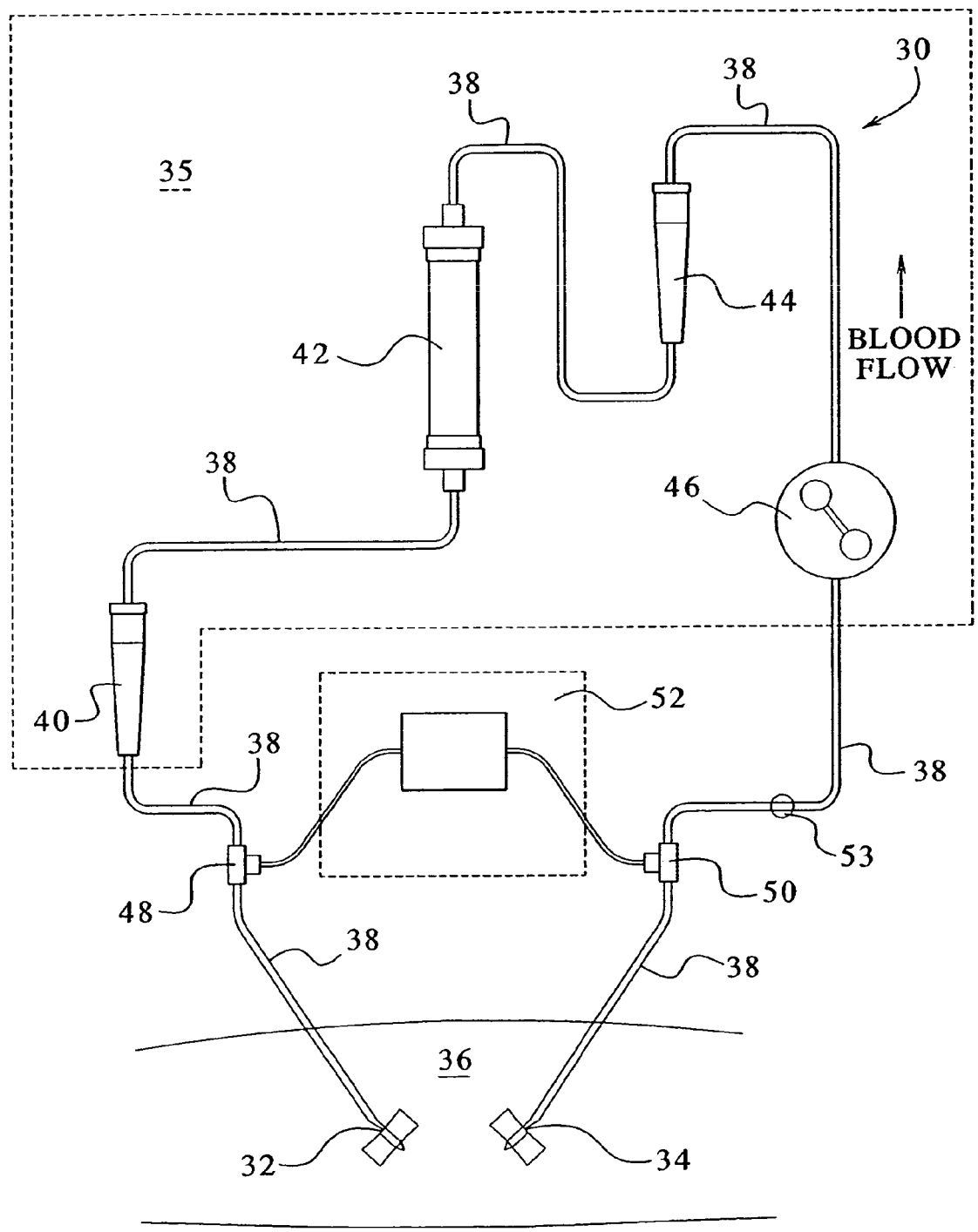
FIG. 1B illustrates a schematic view of an embodiment of the present invention capable of detecting needle dislodgment during dialysis therapy.

As illustrated in FIG. 1B, an embodiment of an apparatus 30 of the present invention is shown as applied during dialysis therapy. In an embodiment, the present invention includes a venous needle 32 and arterial needle 34 inserted within a patient access 36. The venous needle 32 and arterial needle 34 are connected to the dialysis system 35 via a number of tube members 38 that connect the various components of the dialysis system 35 including, for example, a venous drip chamber 40, a dialyzer 42, an arterial drip chamber 44 and a blood pump 46. It should be appreciated that one or more of the components of the dialysis system can be provided within a dialysis machine coupled to the blood circuit. As shown in FIG. 1B, a first electrical contact coupling device 48 and a second electrical contact coupling device 50 are positioned between the dialysis system 35 and the venous needle 32 and the arterial needle 34. As used herein, the term "electrical contact coupling device," "coupling device" or other like terms means any suitable device that can be used to connect an electrical contact to the fluid circuit. In an embodiment, the electrical contact coupling device can be used to contact the electric contact to the fluid circuit allowing fluid contact and electrical connection with the fluid flowing through the fluid circuit as described below.

In an embodiment, the electrical contact pair, preferably an electrode pair, are connected to a controller 52 or other suitable electronic device. The controller can be used to inject an electric signal via the electrode pair and into the blood and/or other fluid as it flows through the blood circuit. This provides a conductor loop along which changes in electrical parameters or values can be measured. The controller 52 which is coupled to the electrode pair can also be used to measure this change. It should be appreciated that the controller can include a single electronic device or any suitable number of devices in electrical connection with the electrical contacts to input an electrical signal into the blood circuit thereby defining a conductor loop, to measure a change in an electrical parameter or value associated with the conductor loop and/or perform any other suitable tasks, such as processing the detectable signal as discussed below.

Preferably, the electrical signal is generated from a constant current that is supplied to the electrodes until dislodgment occurs. The voltage across an unknown impedance of the fluid (e.g., blood) circulating through the blood circuit can then be measured (not shown) to detect a change in impedance due to changes in access conditions. However, it should be appreciated that any suitable electrical parameter and changes thereof can be monitored to detect needle drop-out or the like as previously discussed.

As demonstrated below, the detection capabilities of the present invention are highly sensitive, specific and virtually immediate in response to access disconnection, such as needle dislodgment. Further, the electronic circuit of the present invention is relatively simple in design such that preferably one electrode pair is necessary to conduct direct conductivity measurement. This can reduce costs and effort as compared to known vascular access monitoring techniques that only employ non-invasive detection techniques, such as, capacitive couplers and induction coils as previously discussed.

Applicants have discovered that the total impedance measured ("Z") can be modeled as two lumped impedances in parallel with one impedance ("ZD") being produced by the pump segment, the dialyzer, the drip chambers and/or other suitable components of the dialysis system and/or the like. The other impedance component ("ZP") is formed by the patient's vascular access and associated tubing which carries blood to and from the vascular access and/or the like. In this regard, the total impedance measured can be characterized as a function of both ZD and ZP as follows:

$$Z=(1/ZD+1/ZP)-1$$

Despite this parallel impedance, applicants have discovered that the electrical contacts in connection with the controller can be used to measure a change in impedance along the conductor loop as blood flows through the blood circuit in response to access disconnection, such as needle dislodgment. If needle dislodgment occurs, the conductor loop along at least a portion of the fluid circuit changes from a closed circuit to an open circuit and thus Z=ZD where ZP approaches infinity. In this regard, the direct conductive measurement capabilities of the present invention can be effectively used to detect access disconnection.

Applicants note that the ZD component can produce a level of electrical interference associated with the time-varying high impedance of the components of a medical system coupled to the fluid circuit, such as a dialysis system and its components including, for example, a blood pump, a drip chamber and/or the like. Applicants have discovered that the interference due to the ZD component can be effectively eliminated, or at least reduced, if necessary. In an embodiment, the signal associated with the detection of Z or the like can be further processed as discussed below. Alternatively, in an embodiment, the electrical circuit of the present invention can be designed to block or bypass one or more components of the dialysis system from the conductor loop or pathway defined along the blood circuit as described below. In this regard, the accuracy, sensitivity and responsiveness with respect to the detection of access disconnection can be enhanced.

In an embodiment, a third electrical contact point 53 can be utilized to minimize or effectively eliminate the interferences with respect to the high impedance components coupled to the blood circuit, such as the blood pump and the like. The additional contact point can be made in any suitable way. For example, the third contact point can be an electrode or other suitable device through which electrical continuity can be established between it and one of the electrodes of the coupling devices. In an embodiment, the third electrical contact can be attached to a fluid circuit in fluid and electrical communication with fluid flowing through same.

The third contact point 53 can be positioned at any suitable position along the blood circuit. Preferably, the third contact point 53 is positioned at any suitable location between the blood pump 46 and the coupling device 50 as shown in FIG. 1B. An equalization potential can then be applied between the third contact point 53 and the electrode of the coupling device 50. The potential is applied at a voltage that is equal to the potential applied between the electrodes of the first coupling device 48 and the second coupling device 50.

This effectively causes the electric current or the like, once injected into the blood circuit, to bypass one or more of the components of the dialysis system. In an embodiment, the third contact point 53 can be positioned such that the electric current or the like would effectively bypass all of the components of the dialysis system as shown in FIG. 1B.

Single Access Disconnection

The electrical contacts of the present invention can be positioned in any suitable location relative to the needle, needles or suitable access device inserted within the patient. As illustrated in FIG. 1C, an embodiment of the present invention as applied with respect to the detection of access detection, such as the dislodgment of a single access device inserted within the patient is shown. This type of application is applicable to a variety of different and suitable medical therapies administered via a single access device, such as a single needle, including intravenous infusion and dialysis therapy including hemodialysis, hemofiltration, hemodiafiltration and continuous renal replacement.

As applied, an electrically conductive fluid, such as blood, a blood product, a medical fluid or the like flows between the patient and a fluid system via a single access device. Dislodgment detection of a single access device can include, for example, the detection of needle dislodgment during the delivery of any suitable and electrically conductive fluid or fluids including, for example, blood or medical drug or solution (i.e., a medication contained in an electrically conductive fluid, such as saline), processed blood, blood products, intravenous solutions, the like or combinations thereof. The fluid delivery can be made between an suitable container, such as blood bags or like fluid delivery devices, and a patient. In this regard, immediate and responsive detection of access disconnection via the present invention can be effectively utilized to monitor and control the transfer of blood or a medical fluid, such as a medication or drug, during medical therapy administered via a single needle.

As shown in FIG. 1C, an embodiment of the apparatus or device 54 of the present invention includes an access device 56; such as a needle, inserted into a blood vessel 58 within a needle insertion site 60 of the patient 62. The needle 56 is connected to the fluid system 63, such as a fluid infusion system, via a tube member 64. The infusion system includes, for example, an infusion pump 66 for transferring the blood or the like from a container 68 (e.g., blood bag) to the patient. A first electrical contact 70 is spaced apart from the needle 56 along the tube member 64 and a second electrical contact 72 is attached to the patient near the insertion site 60. The first electrical contact 70 is in fluid contact with the fluid as it flows from the delivery container 68 to the patient.

In this configuration, the first and second electrical contacts, preferably electrodes, can be used to monitor changes in an electrical value, preferably impedance, within a loop formed by at least a portion of the fluid circuit as an electric signal passes therein. The electrical contact points can be coupled to an electronic device 74 which is capable of processing a detectable signal transmitted through the electrodes in response to a change in impedance or the like due to dislodgment of the single access device as described in detail below. Preferably, the electrical signal is generated by a constant current supplied to the electrodes such that a direct conductivity measurement can be conducted to detect a change in impedance or the like in response to changes in vascular access conditions, such as dislodgment of the access needle.

It is believed that the measured impedance, in the single needle application, is a function of both the impedance of the fluid (i.e., blood) and the impedance as measured across the insertion site. In this regard, the electronic device 74 can be adjusted to detect the impedance at the level equivalent to the combined impedance of all items of the electrical path (i.e., the conductive fluid in the tube, needle, blood stream of venous vessel, body tissue, impedance across the skin with respect to the sensing electrode 72 and the like).

Electrical Contacts

As previously discussed, the electrical contacts of the present invention are in fluid contact with the fluid as it flows through the fluid circuit. In this regard, the electrical contacts allow for a direct conductivity measurement which is capable of immediately detecting, with high sensitivity and specificity, a change (e.g., an increase) in impedance or the like due to access disconnection, such as dislodgment of a venous needle (arterial needle or both) from the blood circuit during dialysis therapy.

The electrical contacts can be composed of any suitable conductive and biocompatible material, such as, any suitable electrode material including stainless steel, other suitable conductive materials or combinations thereof. It is essential that the electrode material is biocompatible.

It should be appreciated that the electrical contacts can be constructed in a variety of different shapes and sizes, illustrative examples of which are described below. For example, the electrical contacts can be configured or designed as a plaster electrode which includes an agent capable of expanding when in contact with moisture. The agent can include a variety of suitable materials including gels that are known to expand more than ten times in volume upon contact with moisture.

In an embodiment, the plaster electrode can be utilized to detect fluid (i.e., blood leakage) at an insertion site of an access device insertable within a patient during the administration of medical therapy via a single access device as previously discussed. Upon contact with the fluid, the plaster electrode would necessarily expand to such an extent that the electrode contact is broken, thus causing a detectable increase in impedance of the fluid as it flows from the fluid system to the patient via the needle.

In an embodiment, one or more electrodes (not shown), such as one or more plaster electrodes as previously discussed, can be used in combination with the electrical contact pair as shown, for example, in FIGS. 1A and 1B. For example, a plaster electrode can be attached to the patient near the insertion site of either or both of the arterial and venous needles. In this regard, the plaster electrode(s) can be utilized to detect leakage of fluid, such as blood, from the insertion site of the access device(s).

In an embodiment, an electrode pair is coupled to the blood circuit in an invasive manner (illustrated in FIGS. 2A-2C as discussed below) such that the electrodes contact the blood as previously discussed. An excitation source that includes a constant current source or the like can be applied to the electrodes to inject an electric signal into the blood circuit thereby defining a conductor loop along which direct conductivity measurements can be performed.

To ensure patient safety, the excitation source is typically isolated from the instrument power. Preferably, the excitation source produces a constant electrical current that passes through the blood via the electrodes. Any suitable amount of current can be generated for detection purposes. In an embodiment, the electrical current as it passes through the blood is maintained at a level of about 10 microamperes or less, preferably about 5 microamperes or less. It should be appreciated that the present invention can be operated at low levels of current (e.g., 10 microamperes or less) such that the level of current has negligible, if any, effect on the health and safety of the patient.

It should be appreciated that the impedance or other suitable parameter can be measured and calculated in a variety of different and suitable ways. For example, the amplitude, phase and/or frequency of the constant current excitation source can be measured and varied during the detection of a change in impedance. Impedance levels can then be detected by measuring the voltage across the electrodes In this regard, the amplitude, frequency and/or phase of the voltage can then be measured and utilized in combination with the measured amplitude, frequency and/or phase of the excitation source to calculate blood impedance levels based on derivations or equations which are typically used to calculate impedance.

The electrical contacts can be connected to the blood circuit in a variety of different and suitable ways. For example, the electrical contacts can be an integral component of the extracorporeal system, a disposable component that can be connected and released from the tubing members of the blood circuit, a reusable component that can be autoclaved between uses, or the like.

Electrical Contact Coupling Device

In an embodiment, the apparatus of the present invention includes an electrical contact coupling device that can be utilized to secure the electrical contacts, preferably electrodes, to the blood circuit such that the electrodes effectively contact the blood and, thus, can be used to effectively monitor changes in access conditions as previously discussed. The coupling device of the present invention can also be designed to facilitate the protection of the user against contact with potential electrical sources. In an embodiment, the device can include a conductive element connected to the tube through which a medical fluid, such as blood, can flow wherein the conductive element has a first portion exposed to the medical fluid and a second portion external to the tube.

The coupling device of the present invention can include a variety of different and suitable configurations, components, material make-up or the like. In an embodiment, the present invention can include a device for connecting an electrical contact to a fluid conduit providing fluid and electrical communication between the electrical contact and fluid flowing through the fluid conduit. The device can include a first member including an annular portion capable of accommodating the electrical contact and a first stem portion connected to the annular member wherein the stem portion has an opening extending therethrough to the annular portion; a second member including a base portion with a groove region and a second stem portion with an opening extending therethrough to the groove region allowing the first member to be inserted and secured to the second member; and a contact member adapted to fit the first and second stem portions allowing the contact member to abut against at least a portion of the electrical contact member allowing an electrical connection to be made between the electrical contact and the contact member. Illustrative examples of the electrical contact coupling device of the present invention are described below.

Figure 2A:
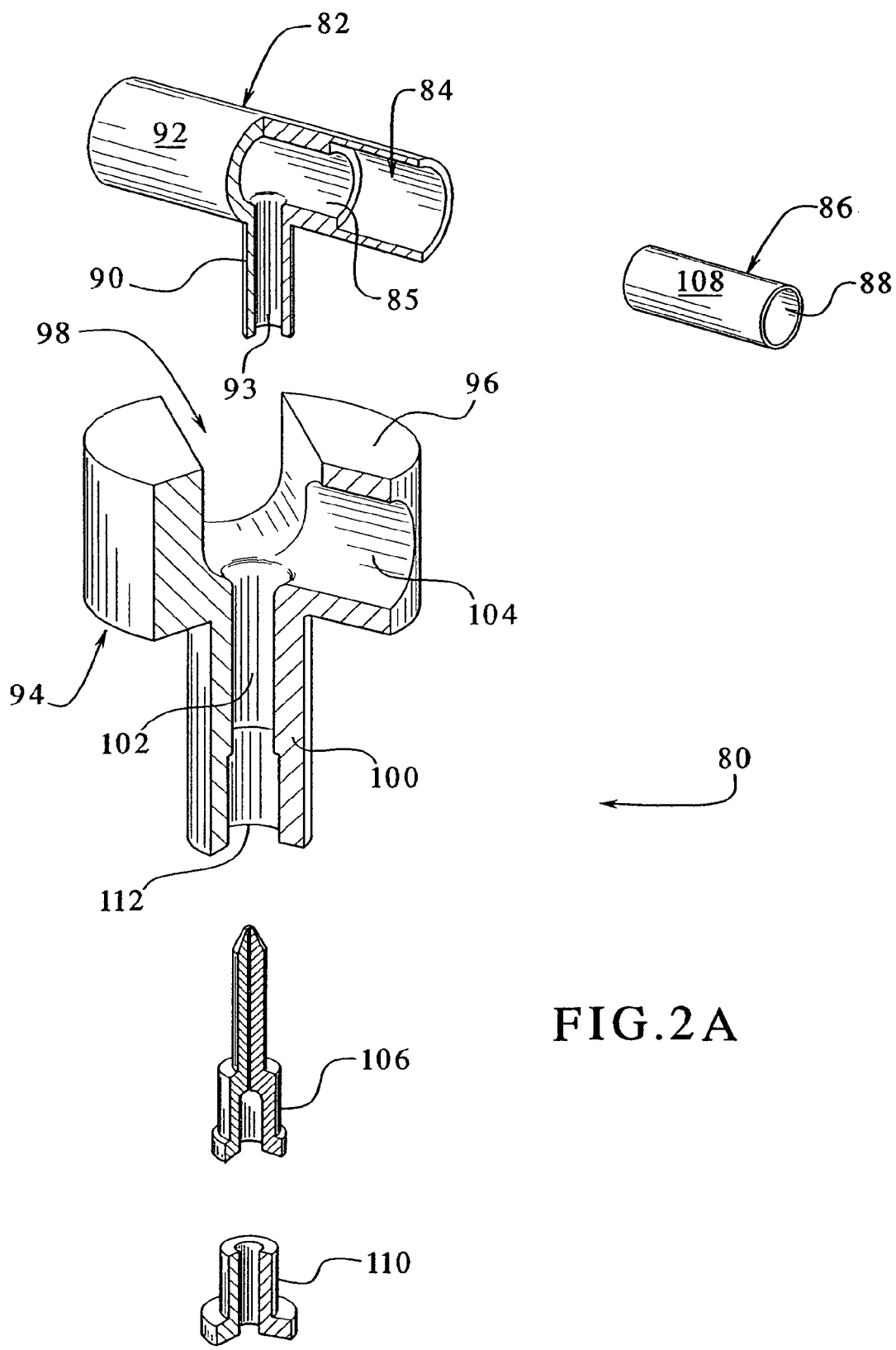
FIG. 2A illustrates an exploded view of an electrical contact coupling device in an embodiment of the present invention.
Figure 2B:
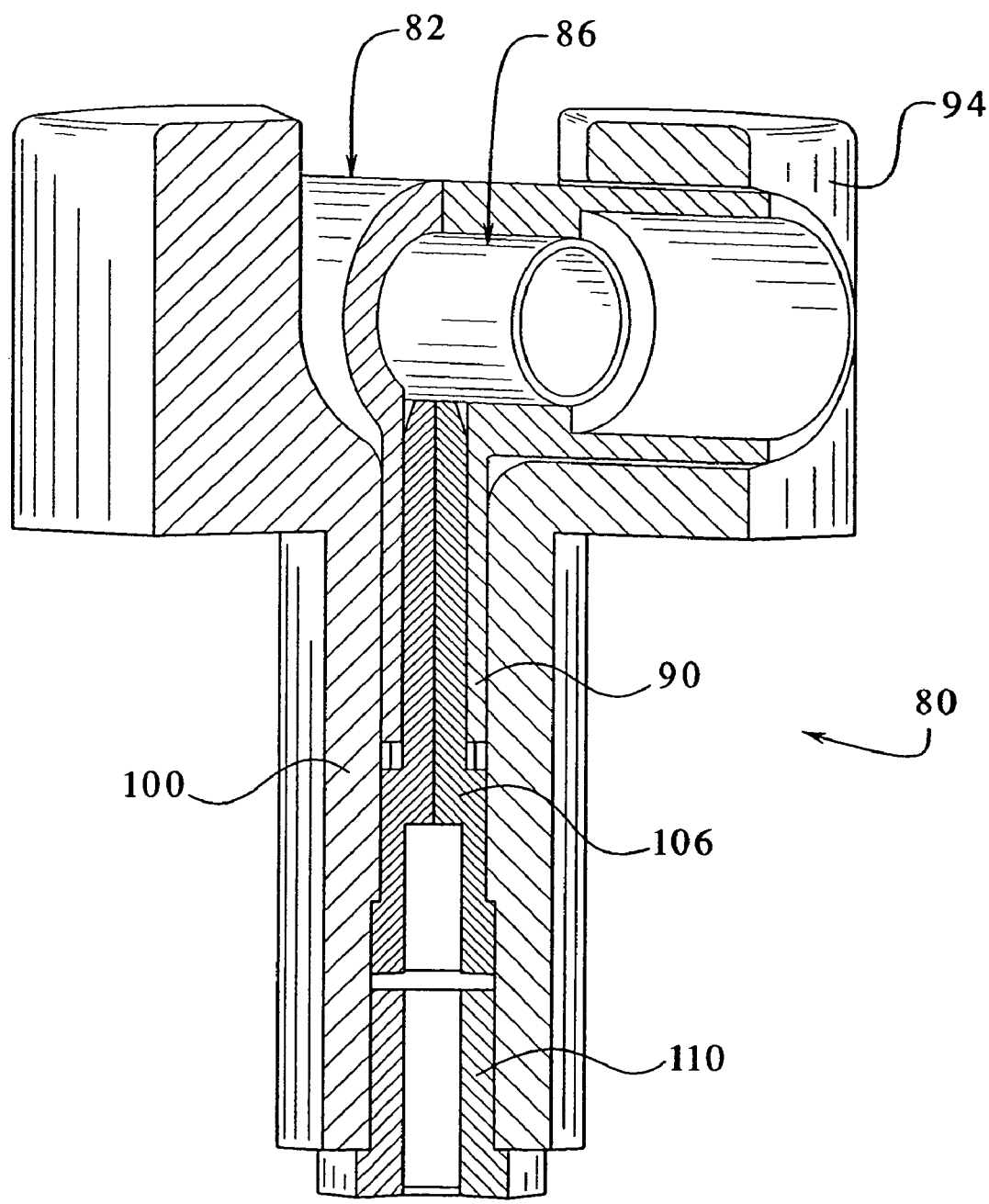
FIG. 2B illustrates a side sectional view of the coupling device of FIG. 2A in an embodiment of the present invention.

As illustrated in FIGS. 2A and 2B, the electrical contact coupling device 80 includes a probe member 82 that has a cylindrical shape with an opening 84 extending therethrough.

In this regard, an electrical contact, preferably an electrode 86 having a cylindrical shape can be inserted into the opening 84 such that the electrode 86 is secure within the probe member 82. In an embodiment, the probe member 82 has a channel 85 extending along at least a portion of the opening 84 within which the electrode 86 can be inserted into the probe member 82. A tube member, for example, from a blood tubing set, connector tube member of a dialysis machine or the like, can be inserted into both ends of the opening 84 of the probe member 82 in contact with an outer portion of the channel 85 allowing blood or other suitable fluid to make fluid contact with the electrode 86 in any suitable manner. The electrode 86 has an opening 88 that extends therethrough within which blood (not shown) or other suitable fluid from the fluid circuit can flow. In an embodiment, the diameter of the opening 88 of the electrode 86 is sized to allow blood flow through the electrode 86 such that blood flow levels under typical operating conditions, such as during dialysis therapy, can be suitably maintained. In this regard, the coupling device of the present invention can be readily and effectively attached to a fluid circuit, including a blood circuit or the like, for use during medical therapy including, for example, dialysis therapy. It should be appreciated that the coupling device 80 of the present invention can be attached to the fluid circuit in any suitable way such that electrical and fluid connection can be made with the fluid flowing through the fluid circuit.

The probe member 82 also includes a stem portion 90 that extends from a surface 92 of its cylindrical-shaped body. The stem portion 90 has an opening 93 that extends therethrough. In an embodiment, the stem portion 90 is positioned such that at least a portion of the electrode 86 is in contact with the opening 93 of the stem portion 90.

In order to secure the electrode 86 to the blood circuit, the coupling device 80 includes a socket member 94 that includes a body portion 96 with an opening 98 for accepting the probe member 82 and for accepting a blood tube member (not shown) of the blood circuit such that blood directly contacts the electrode as it circulates through the blood circuit during dialysis therapy. In an embodiment, the socket member 94 includes a stem portion 100 extending from the body member 96 wherein the stem portion 100 includes an opening 102 extending therethrough. As the probe member 82 is inserted through the opening 98 of the body member 96, the stem portion 90 of the probe member 82 can be inserted into the opening 102 of the stem portion 100 of the body 96 of the socket member 94.

In an embodiment, the socket member 94 includes a groove region 104 extending along at least a portion of the body 96 of the socket member 94. In this regard, the probe member 82 can be inserted through the opening 98 and then moved or positioned into the groove region 104 to secure the probe member 82 within the body 96 of the socket member 94.

In an embodiment, the coupling device 80 includes an electrical contact member 106 that is inserted within the opening 102 of the stem portion 100 of the body 96 of the socket member 94 such that the electrical contact member 106 extends through the opening 93 of the stem portion 90 of the probe member 82 to contact at least a portion of a surface 108 of the electrode 86.

The electrical contact member 106 is utilized to connect the electronics (not shown) of, for example, the excitation source, a signal processing device, other like electronic devices suitable for use in monitoring and/or controlling changes in access conditions, such as needle dislodgment. The electrical contact member 106 can be made of any suitable material, such as any suitable conductive material including, stainless steel, other like conductive materials or combinations thereof. In order to secure the electrical contact member 106 in place, a contact retainer member 110 is inserted within the opening 102 of the stem portion 100 at an end region 112 thereof.

In an embodiment, the coupling device is mounted to a dialysis machine, device or system in any suitable manner. For example, the coupling device can be mounted as an integral component of the dialysis machine. As well, the coupling device can be mounted as a separate and/or stand alone component which can interface with any of the components of the apparatus and system of the present invention. In an embodiment, the coupling device 80 can be insertably mounted via the stem portion 100 of the socket member 94 to a dialysis machine or other suitable components.

Figure 2C:
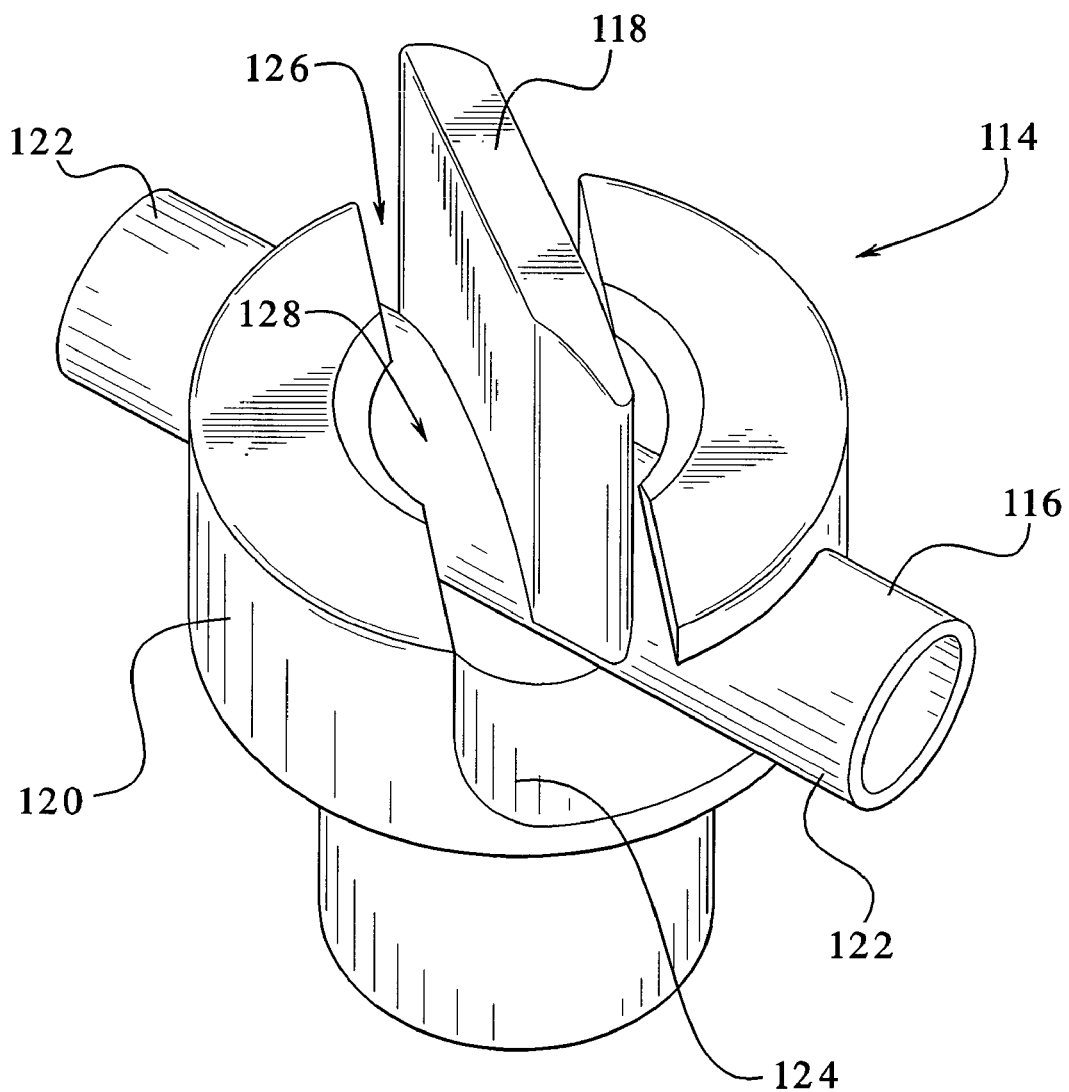
FIG. 2C illustrates another embodiment of the coupling device of the present invention.

It should be appreciated that the electrical contact coupling device can include a variety of different and suitable shapes, sizes and material components. For example, another embodiment of the coupling device is illustrated in FIG. 2C. The coupling device 114 in FIG. 2C is similar in construction to the coupling device as shown in FIGS. 2A and 2B. In this regard, the coupling device 114 of FIG. 2C can include, for example, a cylindrical-shaped electrode or other suitable electrical contact, a probe member for accepting the electrode and securing it in place within a socket member of the sensing device. The probe member includes a stem portion that is insertable within a stem portion of the socket member. An electrical contact member is insertable within the stem portion such that it can contact the electrode. The coupling device of FIG. 2C can also include a contact retainer member to hold the electrical contact member in place similar to the coupling device as shown in FIGS. 2A and 2B.

As shown in FIG. 2C, the probe member 116 of the electrical contact coupling device 114 includes a handle 118 which can facilitate securing the probe member 116 within the socket member 120. The handle 118, as shown, has a solid shape which can facilitate the use and manufacture of the coupling device 114. In addition, the stem portion (not shown) of the probe member 116 is larger in diameter than the stem portion of the probe member as illustrated in FIG. 2A. By increasing the stem size, the probe member can be more easily and readily inserted within the socket member. Further, the probe member is greater in length as compared to the probe member as shown in FIGS. 2A and 2B such that the end regions 122 of the probe member 116 extend beyond a groove region 124 of the socket member 120. This can facilitate securing the probe member within the groove region 124 of the socket member 120.

In an embodiment, an opening 126 of the socket member 120 can include an additional opening portion 128 to accommodate the insertion of the stem portion of the probe member 116, having an increased size, therethrough. This can ensure proper alignment of the probe member with respect to the socket member before insertion of the probe member into the socket member thus facilitating the insertion process.

It should be appreciated that the probe member, socket member and contact retainer member can be composed of a variety of different and suitable materials including, for example, plastics, molded plastics, like materials or combinations thereof. The various components of the coupling device, such as the probe member, socket member and contact retainer member, can be fitted in any suitable way. For example, the components can be fitted in smooth engagement (as shown in FIGS. 2A and 2B), in threaded engagement (as shown in FIGS. 2D and 2E) and/or any suitable fitting engagement or arrangement to one another.

Figure 2D:
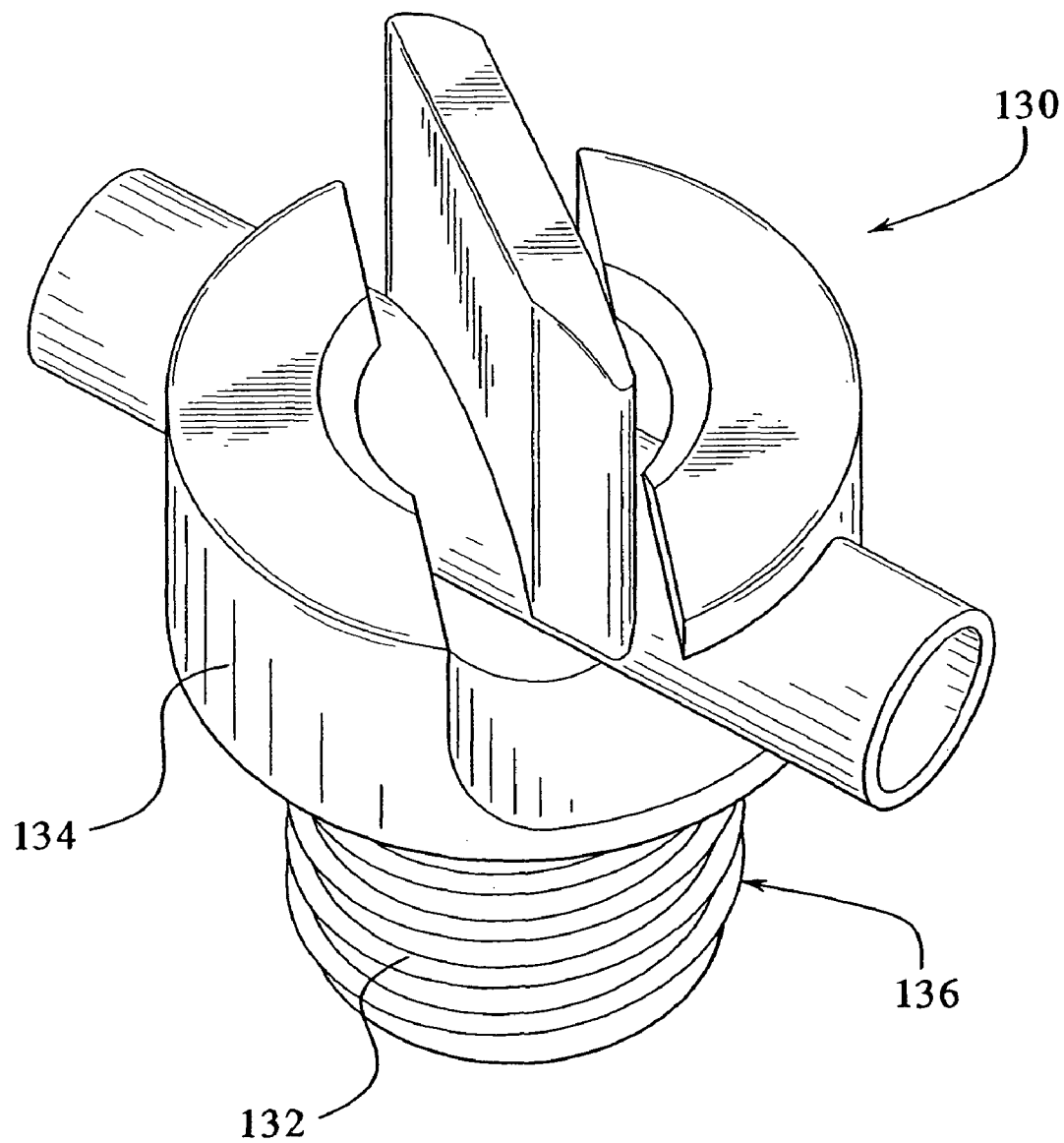
FIG. 2D illustrates another embodiment of the coupling device of the present invention showing a threaded engagement between the components of same.
Figure 2E:
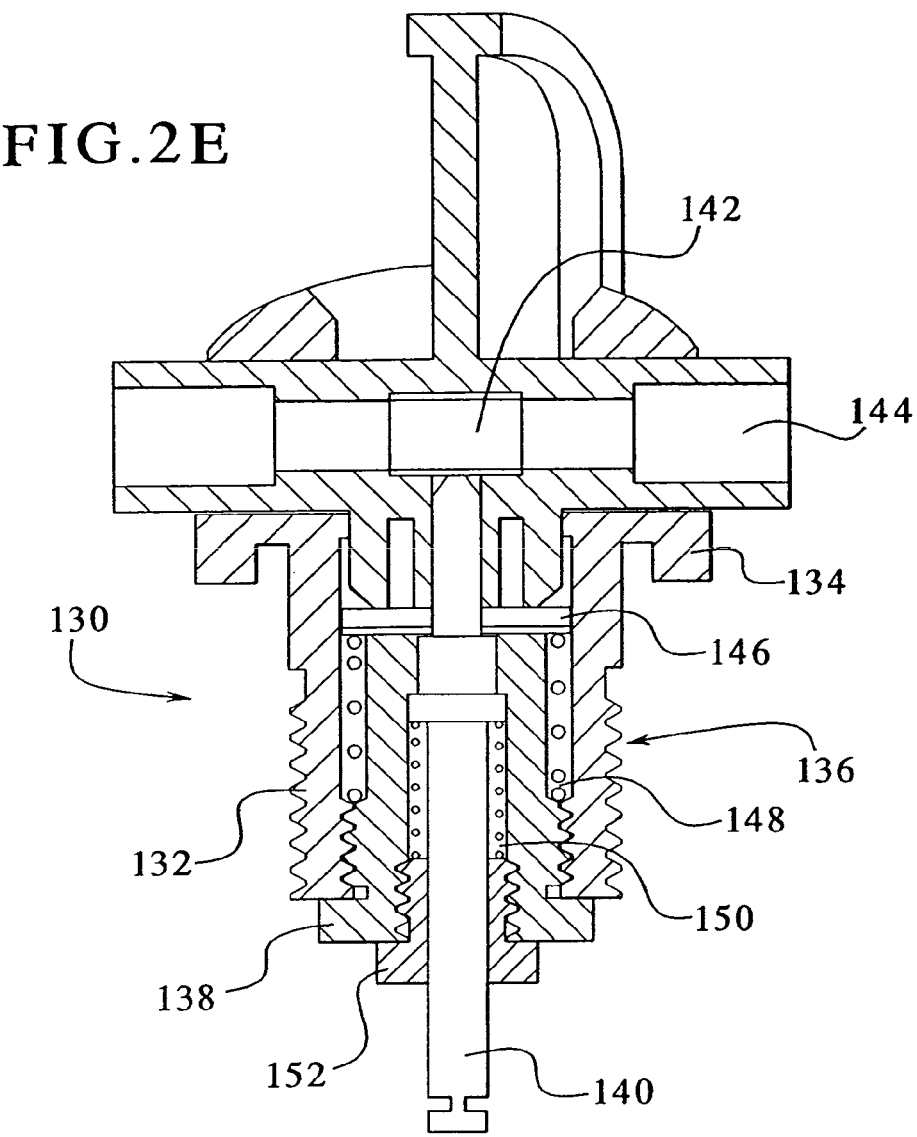
FIG. 2E illustrates a sectional view of FIG. 2D.

As shown in FIGS. 2D and 2E, the coupling device 130 of the present invention can be made of threaded parts which are removably connected to one another to form the coupling device. The threaded parts can facilitate securing the electrode to the blood circuit as well as general use of same as described below.

In an embodiment, the stem portion 132 of the body 134 of the coupling device 130 has a threaded region 136 which can be insertably attached to a dialysis machine or other suitable mounting device in threaded engagement. This can facilitate the ease in which the coupling device is attached and detached from the mounting device.

As shown in FIG. 2E, the stem portion 132 is threaded on both sides allowing it to be in threaded engagement with an annular member 138. The annular member 138 provides direction and support allowing the electrical contact member 140 to abut against the electrode 142 housed in the probe member 144 as previously discussed.

In an embodiment, a plate member 146 made of any suitable conductive material can be depressed against a spring 148 as the probe member 144 is secured to the body 134. At the same time, another spring 150 can be displaced against the electrical contact member 140 in contact with the retainer 152 which is inserted within an annular region of the annular member 138 to secure the electrical contact member 140 to the body 134.

The spring mechanism in an embodiment of the present invention allows the parts of the coupling device 130 to remain in secure engagement during use. It can also facilitate use during detachment of the parts for cleaning, maintenance or other suitable purpose.

In an embodiment, the coupling device can include a device with an electrical contact attached allowing the electrical contact to pierce or puncture the a fluid conduit when the device is movably attached to the fluid conduit. In this regard, the device can act through a clamping mechanism to allow electrical and fluid communication between the electrical contact and fluid flowing through the fluid conduit. The device can be coupled to a controller or the like allowing detection of access disconnection using direct conductive measurement during medical therapy, such as dialysis therapy, as previously discussed. The device can be made in a variety of suitable ways.

Figure 2F:
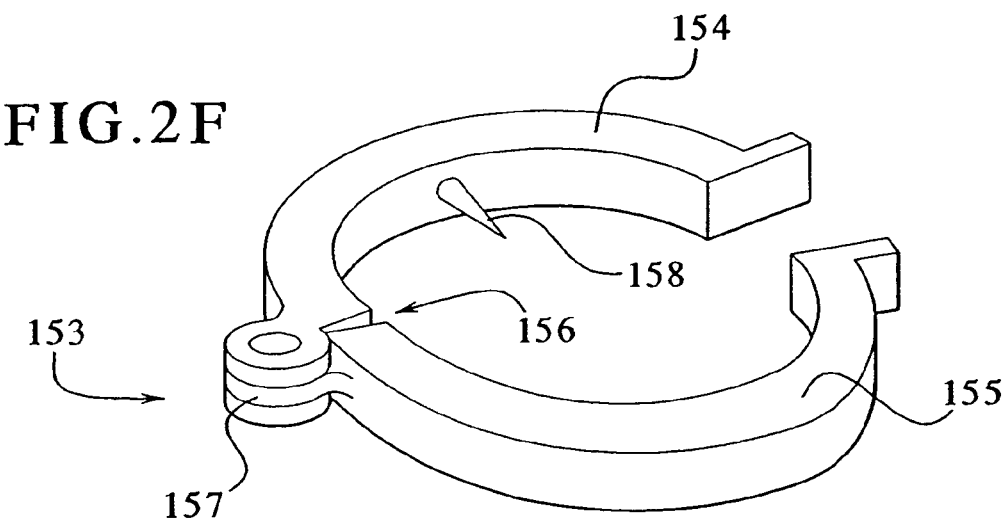
FIG. 2F illustrates another embodiment of a coupling device of the present invention.

In an embodiment, the device 153 includes a first member 154 and a second member 155 movably attached to the first member 154 at an end 156 as shown in FIG. 2F. The first and second members can be attached in any suitable way, such as by a hinge 157 or other suitable mechanism that can allow movement of the first and second members such that the device 153 can be attached to a fluid conduit. The movable members of the device 153 can be composed of any suitable material, preferably a conductive material, such as stainless steel, that is compatible with the electrical contact such that an effective electrical connection can be made.

The electrical contact 158 can be composed of any suitable material, such as stainless steel, as previously discussed. The electrical contact material defines a shape and is attached to a portion of the first or second members in any suitable way. This allows the electrical contact 158 to puncture or pierce a fluid conduit when the device 158 is attached thereto such that the electrical contact 158 can make electrical and fluid contact with fluid flowing through the conduit.

In an embodiment, the device 158 is self-sealing upon attachment to the fluid conduit. This can be done in any suitable way, such as by applying any suitable adhesive, gel or other sealing material to the device 158, if necessary, prior to attachment to the fluid conduit. In this regard, the device 153 provides a simple design that can be effectively and readily used to provide both fluid and electrical contact between an electrical contact and fluid flowing through a fluid conduit, such as a blood circuit.

As previously discussed, the present invention can be effectively utilized to detect dislodgment of an access device, such as a needle, inserted within a patient through which fluid can pass between the patient and a fluid delivery and/or treatment system. The present invention can be applied in a number of different applications, such as medical therapies or treatments, particularly dialysis therapies. In dialysis therapies, access devices, such as needles, are inserted into a patient's arteries and veins to connect blood flow to and from the dialysis machine.

Under these circumstances, if the needle becomes dislodged or separated from the blood circuit, particularly the venous needle, the amount of blood loss from the patient can be significant and immediate. In this regard, the present invention can be utilized to controllably and effectively minimize blood loss from a patient due to dislodgment of the access device, such as during dialysis therapy including hemodialysis, hemofiltration, hemodiafiltration and continuous renal replacement.

Signal Detection and Processing

As previously discussed, the electrical contacts in connection with the controller can be used to detect a change in impedance or the like in response to needle drop-out or other like changes in access conditions. In an embodiment, the present invention can be adapted to correct for any variations in the baseline impedance over time. This can increase the level of sensitivity with respect to the detection capabilities of the present invention. In this regard, if changes in the baseline impedance are too great and not adequately corrected for, changes in impedance due to needle dislodgment may not be as readily, if at all, detectable above baseline values.

From a practical standpoint, there are a number of different process conditions that may influence a change in the baseline impedance over time. For example, a gradual drift or change in the baseline can occur due to a change in the characteristics, such as the hematocrit, plasma protein, blood/water conductivity and/or the like, of the blood or other suitable fluid during treatment. This can arise due to changes in the level of electrolytes or other components during dialysis therapy.

Figure 3:
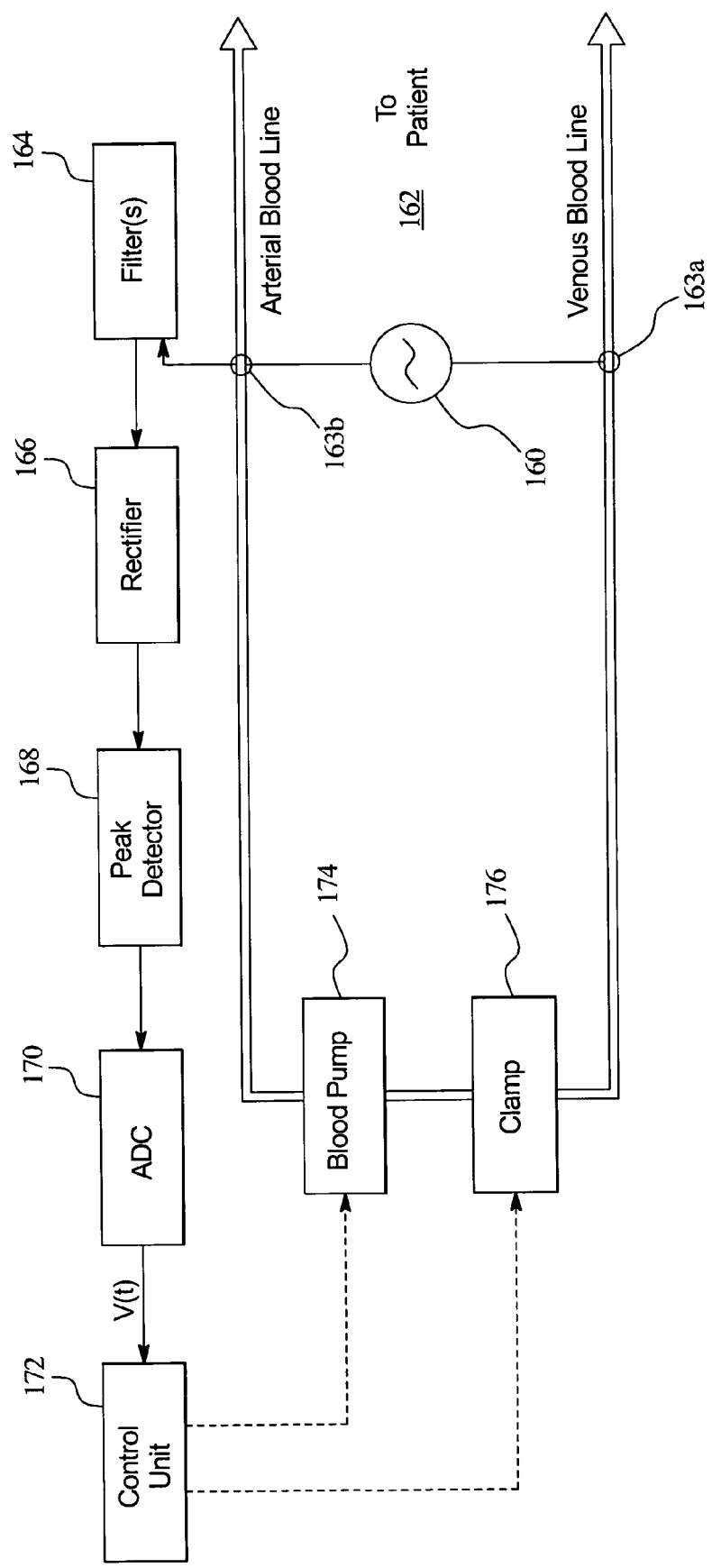
FIG. 3 schematically illustrates an embodiment of the present invention relating to processing of a measurable voltage signal to correct for changes in baseline impedance during treatment.

As illustrated in FIG. 3, the present invention can process a measurable voltage signal to correct for changes in baseline impedance over time. This can enhance the detection capabilities of the present invention as previously discussed. In an embodiment, a current source 160 or the like generates an electric current to pass through the blood as it circulates into, through and out of the patient along the extracorporeal blood circuit 162 which connects the patient via venous and arterial needles to the dialysis system including a variety of process components. The electric current is injected into the blood circuit via a first electrical contact 163a thereby defining a conductor loop or pathway along the blood circuits. Preferably, the current is maintained at a constant level until dislodgment occurs. The second electrode 163b is used to sense voltage or the like along the conductor loop and then pass a signal indicative of same and/or changes thereof to an electronic device for detection and processing as previously discussed. The voltage signal can be measured and processed in any suitable manner.

In an embodiment, the signal is passed through a series of components including a filter or filters 164 which can act to filter noise from the signal, particularly noise derived from the rotation from the pump in order to minimize a false negative and/or positive detection of needle dislodgment, a rectifier 166, a peak detector 168 and an analog to digital converter ("ADC") 170 to digitize the signal. In this regard, the digital signal can then be stored in a computer device (not shown) for further processing. The voltage signal is continually measured and processed over time. With each measurement, the digitized signals are compared to evaluate changes due to baseline changes associated with variations in process conditions over time, such as a change in the characteristics of blood as previously discussed. If a baseline change is determined, the digitized signal can be further processed to correct for the change in baseline.

The voltage data is continually sent to a control unit 172 coupled to the ADC. The control unit continually performs a calculation to determine whether a change in impedance or the like in response to needle dislodgment has occurred. In an embodiment, dislodgment of an access device is detected when $[V(t)-V(t-T)]>C1$, where t is time, where T is the period of blood pump revolution, where C1 is a constant and where $V(t)=Io*Z$, where Io is current and where Z is the impedance of the bloodline which is a function of the impedance associated with patient's vascular access and the impedance associated with various components of the dialysis system, such as the dialyzer, as previously discussed.

If disconnection of the patient from the blood circuit is detected, the control unit 172 can be utilized to process the signal in order to minimize blood loss from the patient. In an embodiment, the controller is in communication with a dialysis system as applied to administer dialysis therapy including, for example, hemodialysis, hemofiltration, hemodiafiltration and continuous renal replacement. This communication can be either hard-wired (i.e., electrical communication cable), a wireless communication (i.e., wireless RF interface), a pneumatic interface or the like. In this regard, the controller can process the signal to communicate with the dialysis system or device to shut off or stop the blood pump 174 associated with the hemodialysis machine and thus effectively minimize the amount of blood loss from the patient due to needle dislodgment during hemodialysis.

The controller can communicate with the dialysis system in a variety of other ways. For example, the controller and hemodialysis machine can communicate to activate a venous line clamp 176 for preventing further blood flow via the venous needle thus minimizing blood loss to the patient. In an embodiment, the venous line clamp is activated by the controller and attached to or positioned relative to the venous needle such that it can clamp off the venous line in close proximity to the needle. Once clamped, the dialysis system is capable of sensing an increase in pressure and can be programmed to shut-off the blood pump upon sensing pressure within the blood flow line which is above a predetermined level. Alternatively, the venous line clamp can be controllably attached to the dialysis system.

In an embodiment, an alarm can be activated upon detection of blood loss due to, for example, needle dislodgment during dialysis therapy. Once activated, the alarm (i.e., audio and/or visual or the like) is capable of alerting the patient, a medical care provider (i.e., doctor, registered nurse or the like) and/or a non-medical care provider (i.e., family member, friend or the like) of the blood loss due to, for example, needle dislodgment. The alarm function is particularly desirable during dialysis therapy in a non-medical facility, such as in a home setting or self care setting where dialysis therapy is typically administered by the patient and/or a non-medical care provider in a non-medical setting or environment excluding a hospital or other like medical facility.

In this regard, the alarm activation allows, for example, the patient to responsively act to ensure that the dialysis therapy is terminated by, for example, to check that the blood pump has been automatically shut off to minimize blood loss to the patient. Thus, the patient has the ability to act without the assistance of a third party (i.e., to act on his or her own) to ensure that responsive measures are taken to minimize blood loss. The alarm can thus function to ensure the patient's safety during the administration of dialysis therapy, particularly as applied to home hemo treatments where at least a portion of the dialysis therapy can be administered while the patient is sleeping.

Dialysis Machine

As previously discussed, the present invention can be adapted for use with any suitable fluid delivery system, treatment system or the like. In an embodiment, the present invention is adapted for use with a dialysis machine to detect access disconnection as blood flows between the patient and the dialysis machine along a blood circuit during treatment, including, for example hemodialysis, hemofiltration and hemodiafiltration.

Figure 4A:
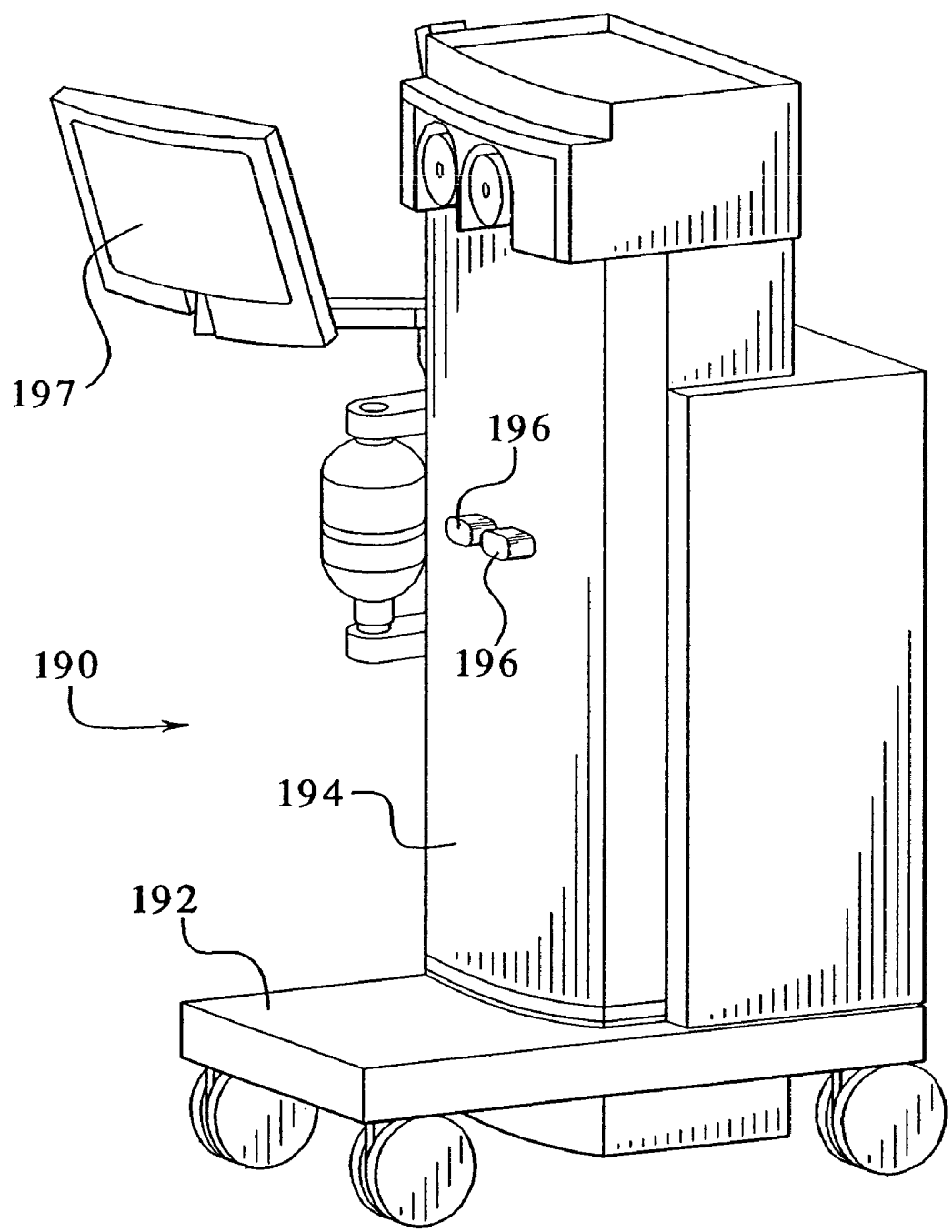
FIG. 4A schematically illustrates a hemodialysis machine in an embodiment of the present invention.

The present invention can include any suitable dialysis machine for such purposes. An example, of a hemodialysis machine of the present invention is disclosed in U.S. Pat. No. 6,143,181 herein incorporated by reference. In an embodiment, the dialysis machine 190 comprises a mobile chassis 192 and it has at the front side 194 thereof with a common mechanism 196 for connecting tubing or the like by which a patient can be connected to the dialysis machine as shown in FIG. 4A. A flat touch screen 197 which can show several operational parameters and is provided with symbols and fields for adjustment of the dialysis machine by relevant symbols and fields, respectively, on the screen being touched can be adjusted vertically and can be universally pivoted on the dialysis machine and can be fixed in the desired adjusted position.

In an embodiment, the dialysis machine includes a chassis having one or more connectors for connecting a patient to the dialysis machine via a blood circuit allowing blood to flow between the patient and the dialysis machine during dialysis therapy wherein one or more electrical contacts are connected to the blood circuit in fluid communication with the blood allowing detection of a change in an electrical value in response to access disconnection as the blood flows through the blood circuit having an electrical signal passing therein.

Figure 4B:
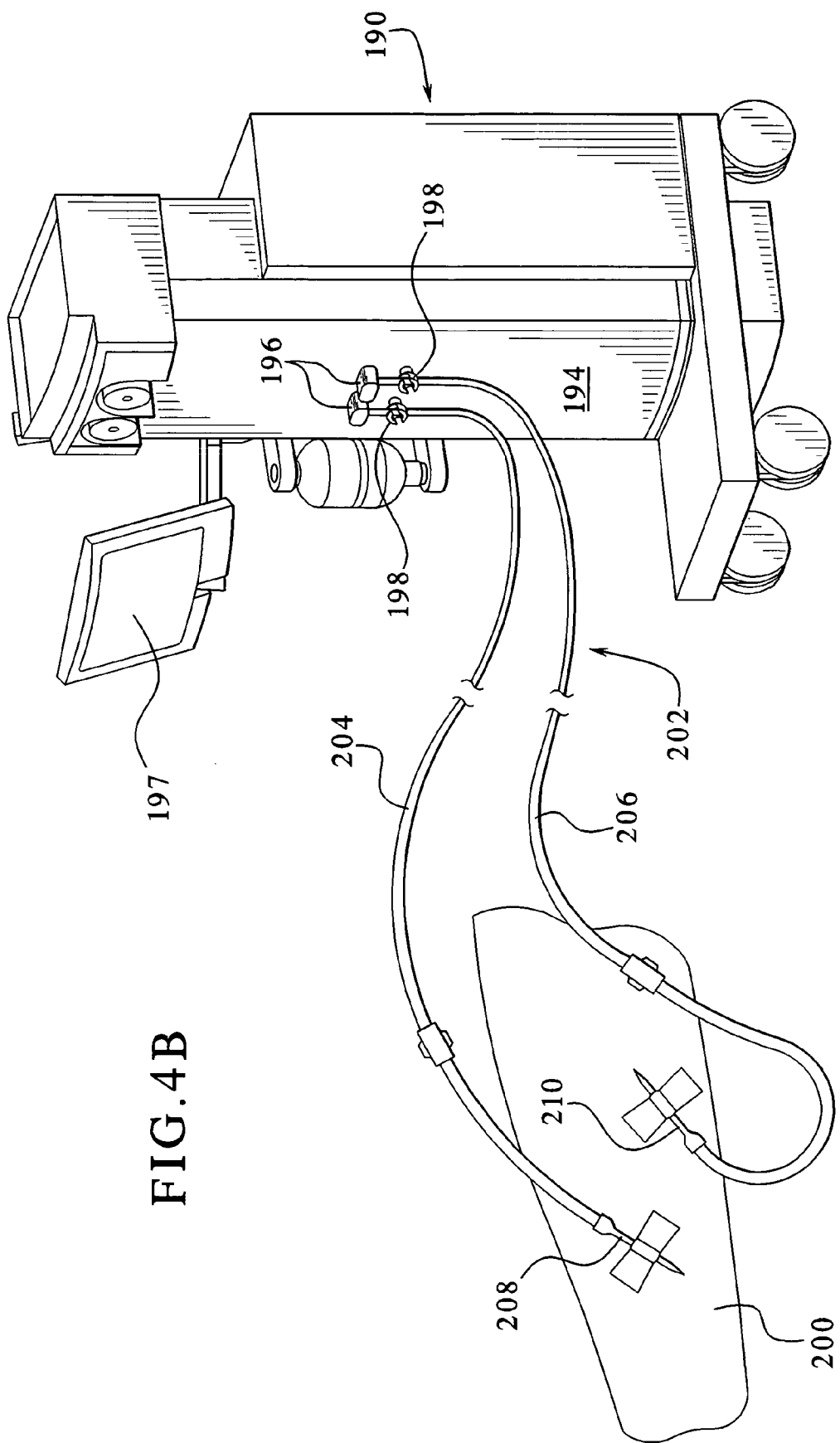
FIG. 4B schematically illustrates a hemodialysis machine coupled to a patient's access via a tubing set in an embodiment of the present invention.

In an embodiment, the dialysis machine of the present invention can be designed to accommodate one or more of the electrical contact coupling devices, such as a pair of coupling device, used to detect access disconnection as shown in FIG. 4B. For example, one or more coupling devices 198 can be attached to the front panel 194 of the dialysis machine 190. This can be done in any suitable way. In an embodiment, the a stem portion of the coupling device is insertably mounted via a threaded fit, frictional fit or the like, as previously discussed. This connects the patient to the dialysis machine 190 via a blood tubing set 202. The blood tubing set includes a first blood line 204 and a second blood line 206. In an embodiment, the first blood line 204 is connected to the patient via an arterial needle 208 or the like through which blood can flow from the patient 200 to the dialysis machine 190. The second blood line 206 is then connected to the patient 200 via a venous needle 210 or the like through which fluid flows from the dialysis machine to the patient thereby defining a blood circuit. Alternatively, the first blood line and the second blood line can be coupled to the venous needle and the arterial needle, respectively. The blood lines are made from any suitable medical grade material. In this regard, access disconnection, such as dislodgment of an arterial needle and/or a venous needle can be detected as previously discussed. Alternatively, the coupling device can be attached to the blood tubing set which is then attached to the dialysis machine in any suitable way.

Dialysis Treatment Centers

As previously discussed, the present invention can be used during dialysis therapy conducted at home and in dialysis treatment centers. The dialysis treatment centers can provide dialysis therapy to a number of patients. In this regard, the treatment centers include a number of dialysis machines to accommodate patient demands. The therapy sessions at dialysis treatment centers can be performed 24 hours a day, seven days a week depending on the locale and the patient demand for use.

In an embodiment, the dialysis treatment centers are provided with the capability to detect access disconnection during dialysis therapy pursuant to an embodiment of the present invention. For example, one or more of the dialysis machines can be adapted for use with an electrical contact coupling device along with the necessary other components to detect access disconnection as previously discussed.

In an embodiment, the electrical contact coupling device can be directly attached to one or more of the dialysis machines of the dialysis treatment center. It should be appreciated that the apparatuses, devices, methods and/or systems pursuant to an embodiment of the present invention can be applied for use during dialysis therapy administered to one or more patients in the dialysis treatment center in any suitable way. In an embodiment, the treatment center can have one or more patient stations at which dialysis therapy can be performed on one or more patients each coupled to a respective dialysis machine. Any suitable in-center therapy can be performed including, for example, hemodialysis, hemofiltration and hemodiafiltration and combinations thereof. As used herein, the term "patient station" or other like terms mean any suitably defined area of the dialysis treatment center dedicated for use during dialysis therapy. The patient station can include any number and type of suitable equipment necessary to administer dialysis therapy.

In an embodiment, the dialysis treatment center includes a number of patient stations each at which dialysis therapy can be administered to one or more patients; and one or more dialysis machines located at a respective patient station. One or more of the dialysis machines can include a chassis having one or more connectors for connecting a patient to the dialysis machine via a blood circuit allowing blood to flow between the patient and the dialysis machine during dialysis therapy wherein a pair of electrical contacts are connected to the blood circuit in fluid communication with the blood allowing detection of a change in an electrical value in response to access disconnection as the blood flows through the blood circuit having an electrical signal passing therein.

As previously discussed, the access disconnection detection capabilities of the present invention can be utilized to monitor and control a safe and effective dialysis therapy. Upon dislodgment of an access device, such as a needle, from the patient, the direct conductive measurement capabilities of the present invention can be used to provide a signal indicative of dislodgment that can be further processed for control and/or monitoring purposes. In an embodiment, the signal can be further processed to automatically terminate dialysis therapy to minimize blood loss due to dislodgment as previously discussed. Further, the signal can be processed to activate an alarm which can alert the patient and/or medical personnel to the dislodgment condition to ensure that responsive measures are taken. It should be appreciated that the present invention can be modified in a variety of suitable ways to facilitate the safe and effective administration of medical therapy, including dialysis therapy.

Applicants have found that the direct conductive measurement capabilities of the apparatus of the present invention can immediately detect blood loss or the like due to access disconnection, such as needle dislodgment, with high sensitivity and selectivity such that responsive measures can be taken to minimize blood loss due to same. The ability to act responsively and quickly to minimize blood loss upon detection thereof is particularly important with respect to needle dislodgment during hemodialysis. If not detected and responded to immediately, the amount of blood loss can be significant. In an embodiment, the present invention is capable of taking active or responsive measures, to minimize blood loss (i.e., shut-off blood pump, activate venous line clamp or the like) within about three seconds or less, preferably within about two to about three second upon immediate detection of needle dislodgment.

In addition, the controller can be utilized to monitor and/or control one or more treatment parameters during hemodialysis. These parameters can include, for example, the detection of blood due to blood loss upon needle dislodgment, the change in blood flow, the detection of air bubbles in the arterial line, detection of movement of the sensor during treatment, detection and/or monitoring of electrical continuity of the sensor or other like treatment parameters. In an embodiment, the controller includes a display (not shown) for monitoring one or more of the parameters.

As used herein "medical care provider" or other like terms including, for example, "medical care personnel", means an individual or individuals who are medically licensed, trained, experienced and/or otherwise qualified to practice and/or administer medical procedures including, for example, dialysis therapy, to a patient. Examples of a medical care provider include a doctor, a physician, a registered nurse or other like medical care personnel.

As used herein "non-medical care provider" or other like terms including, for example, "non-medical care personnel" means an individual or individuals who are not generally recognized as typical medical care providers, such as doctors, physicians, registered nurses or the like. Examples of non-medical care providers include patients, family members, friends or other like individuals.

As used herein "medical facility" or other like terms including, for example, "medical setting" means a facility or center where medical procedures or therapies, including dialysis therapies, are typically performed under the care of medical care personnel. Examples of medical facilities include hospitals, medical treatment facilities, such as dialysis treatment facilities, dialysis treatment centers, hemodialysis centers or the like.

As used herein "non-medical facility" or other like terms including, for example, "non-medical setting" means a facility, center, setting and/or environment that is not recognized as a typical medical facility, such as a hospital or the like. Examples of non-medical settings include a home, a residence or the like.

It should be appreciated that the electrode output signal can be combined with other less sensitive blood loss detection methods, such as venous pressure measurements, systemic blood pressure, the like or combinations thereof, to improve specificity to needle dislodgment.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. An extracorporeal blood system comprising:
   an extracorporeal blood machine including an extracorporeal blood circuit;
   an access device enabling the extracorporeal blood circuit to be connected to a patient;
   a pair of electrical contacts configured to contact blood as the blood flows through the extracorporeal blood circuit; and
   a controller configured to model a total impedance Z according to at least two lumped impedances including (i) a lumped impedance $Z_D$ due to components of the extracorporeal blood machine and (ii) a lumped impedance $Z_P$ due to access of the extracorporeal blood circuit to the patient.

2. The extracorporeal blood system of claim 1, wherein $Z_P$ is due at least to the access device and tubing associated with the extracorporeal blood circuit.

3. The extracorporeal blood system of claim 1, wherein $Z_D$ is due at least to a pump, dialyzer and drip chambers.

4. The extracorporeal blood system of claim 1, wherein the controller is configured to assume $Z_P$ approaches infinity upon dislodgment of the access device from the patient, such that Z becomes at least substantially equal to $Z_D$.

5. The extracorporeal blood system of claim 1, wherein an electrical contact coupling device is coupled to the extracorporeal blood circuit.

6. The extracorporeal blood system of claim 5, which includes a conductive device including a first member and a second member movably attached to the first member allowing for displacement of the first member and the second member into an open arrangement and a closed arrangement.

7. The extracorporeal blood system of claim 6, wherein the conductive device includes a hinge attached to the first member and the second member at the end.

8. The extracorporeal blood system of claim 5, wherein at least a portion of each of the first and second members is made of a material compatible with an electrical contact provide on the conductive device such that an effective electrical connection can be made.

9. The extracorporeal blood system of claim 1, wherein the extracorporeal blood machine is of a type selected from the group consisting of:
   hemodialysis, hemofiltration, hemodiafiltration and continuous renal replacement therapy.

* * * * *